US 10,532,116 B2

(12) United States Patent
Cauley

(10) Patent No.: US 10,532,116 B2
(45) Date of Patent: Jan. 14, 2020

(54) PROCESSING UNIT AND METHOD FOR SEPARATING HYDROCARBONS FROM FEEDSTOCK MATERIAL

(71) Applicant: FULCRUM ENERGY CORPORATION, Edmonton (CA)

(72) Inventor: Phillip Cauley, Flint, TX (US)

(73) Assignee: FULCRUM ENERGY CORPORATION, Edmonton (CA)

( * ) Notice: Subject to any disclaimer, the term of this patent is extended or adjusted under 35 U.S.C. 154(b) by 0 days.

(21) Appl. No.: 15/480,595

(22) Filed: Apr. 6, 2017

(65) Prior Publication Data

US 2017/0333581 A1     Nov. 23, 2017

Related U.S. Application Data

(63) Continuation of application No. 14/396,892, filed as application No. PCT/CA2013/050318 on Apr. 25, 2013, now abandoned.

(30) Foreign Application Priority Data

Apr. 25, 2012   (CA) .................................... 2775338

(51) Int. Cl.
*A61L 2/10*        (2006.01)
*F21V 21/00*       (2006.01)
(Continued)

(52) U.S. Cl.
CPC ................ *A61L 2/10* (2013.01); *C10G 1/045* (2013.01); *C10G 31/06* (2013.01); *F21V 21/00* (2013.01)

(58) Field of Classification Search
None
See application file for complete search history.

(56) References Cited

U.S. PATENT DOCUMENTS

| 278,516 A | 5/1883 | Floyd |
|---|---|---|
| 4,077,868 A | 3/1978 | Chambers |

(Continued)

FOREIGN PATENT DOCUMENTS

| CA | 2599741 | 2/2008 |
|---|---|---|
| CH | 703609 | 2/2012 |
| GB | 2140029 | 11/1984 |

OTHER PUBLICATIONS

International Search Report dated Aug. 21, 2013, in PCT/CA2013/050318, filed Apr. 25, 2013.

(Continued)

*Primary Examiner* — Tam M Nguyen
(74) *Attorney, Agent, or Firm* — Hovey Williams LLP

(57) ABSTRACT

A processing unit and method for separating hydrocarbons from feedstock material. The processing unit includes at least one rotating conveyor in communication with a material inlet and a material outlet; a vacuum pump providing a vacuum atmosphere within the rotating conveyor; at least one material transfer device positioned at the material inlet and at least one material transfer device positioned at the material outlet, each material transfer device configured to allow transfer of feedstock material into or out of the rotating conveyor whilst maintaining the vacuum atmosphere within the rotating conveyor; and an electrostatic generator connected to the rotating conveyor providing a static charge to the vacuum atmosphere within the rotating conveyor. The method includes rotating the feedstock material in at least one rotating conveyor in communication with a material inlet and a material outlet; providing a vacuum atmosphere within the rotating conveyor; providing a static charge to the vacuum atmosphere within the rotating conveyor; transferring the feedstock material into and out of the rotating conveyor through at least one material transfer device positioned at the material inlet and at least one (Continued)

material transfer device positioned at the material outlet, each material transfer device allowing transfer of feedstock material into or out of the rotating conveyor whilst maintaining the vacuum atmosphere within the rotating conveyor.

20 Claims, 13 Drawing Sheets

(51) Int. Cl.
*C10G 1/04* (2006.01)
*C10G 31/06* (2006.01)

(56) References Cited

U.S. PATENT DOCUMENTS

| | | | |
|---|---|---|---|
| 6,226,889 | B1 | 5/2001 | Aulbaugh et al. |
| 7,621,226 | B2 | 11/2009 | Cauley et al. |
| 7,641,770 | B2 | 1/2010 | Cauley et al. |
| 2007/0181465 | A1 | 8/2007 | Collette |
| 2008/0096787 | A1 | 4/2008 | Cauley et al. |
| 2008/0053813 | A1 | 6/2008 | Cauley |
| 2010/0024696 | A1 | 2/2010 | Cauley et al. |
| 2010/0147671 | A1 | 6/2010 | Cauley et al. |
| 2015/0118101 | A1* | 4/2015 | Cauley ............... C10G 31/06 422/6 |
| 2016/0045841 | A1* | 2/2016 | Kaplan ............... B01J 19/0093 429/49 |
| 2016/0251099 | A1* | 9/2016 | Poppi ............... A61L 2/087 250/454.11 |

OTHER PUBLICATIONS

Office Action issued in Chinese Patent Application No. 201380033204.9.
Office Action dated Mar. 7, 2013, in corresponding Canadian Patent Application 2,775,338.
Extended European Search Report dated Nov. 18, 2015, in EP 13781813.4.
Office Action dated Jul. 3, 2015, in Chinese Patent Application No. 201380033204.9.
International Preliminary Report on Patentability dated Oct. 28, 2014, in PCT/CA2013/050318, filed Apr. 25, 2013.

\* cited by examiner

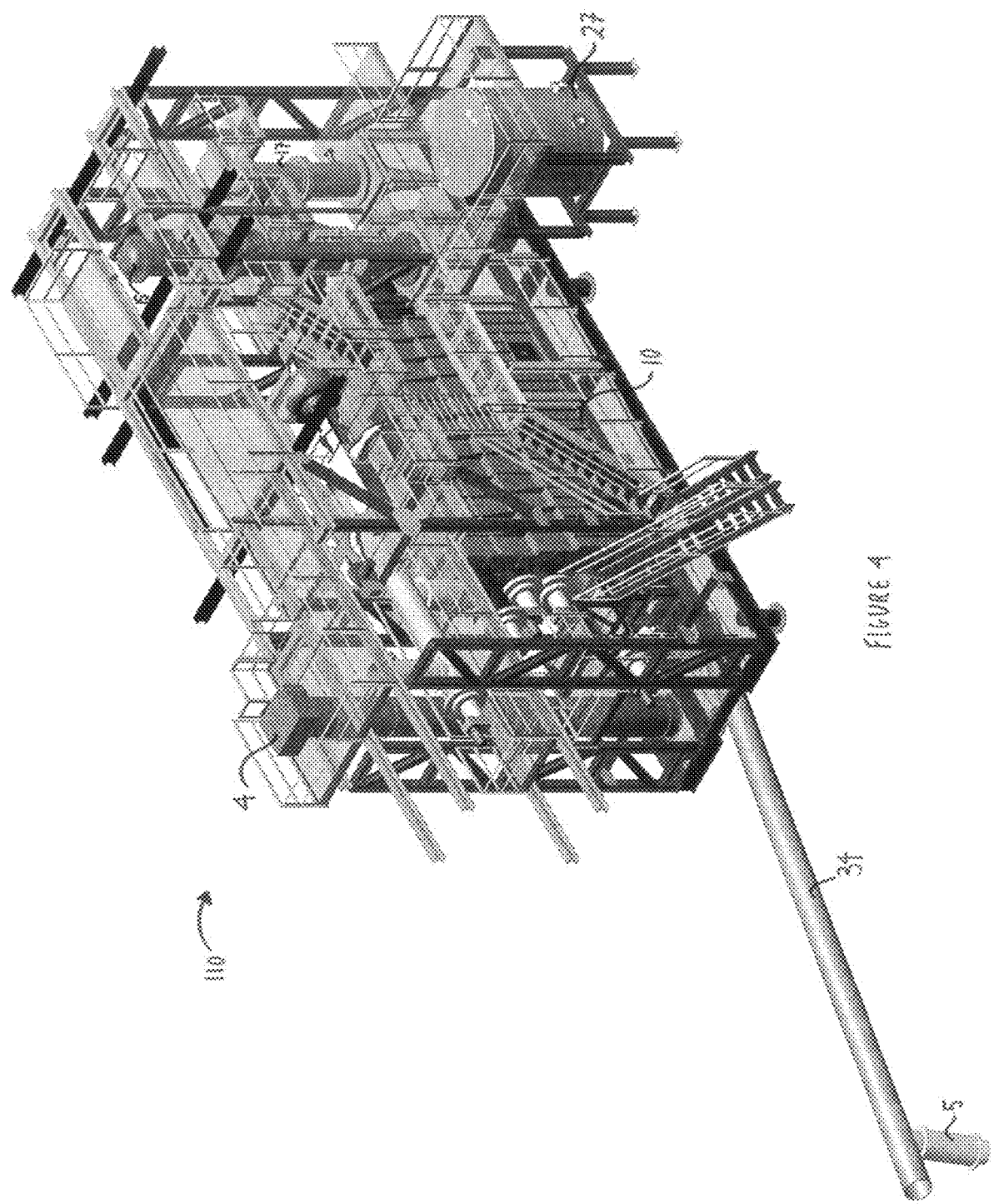

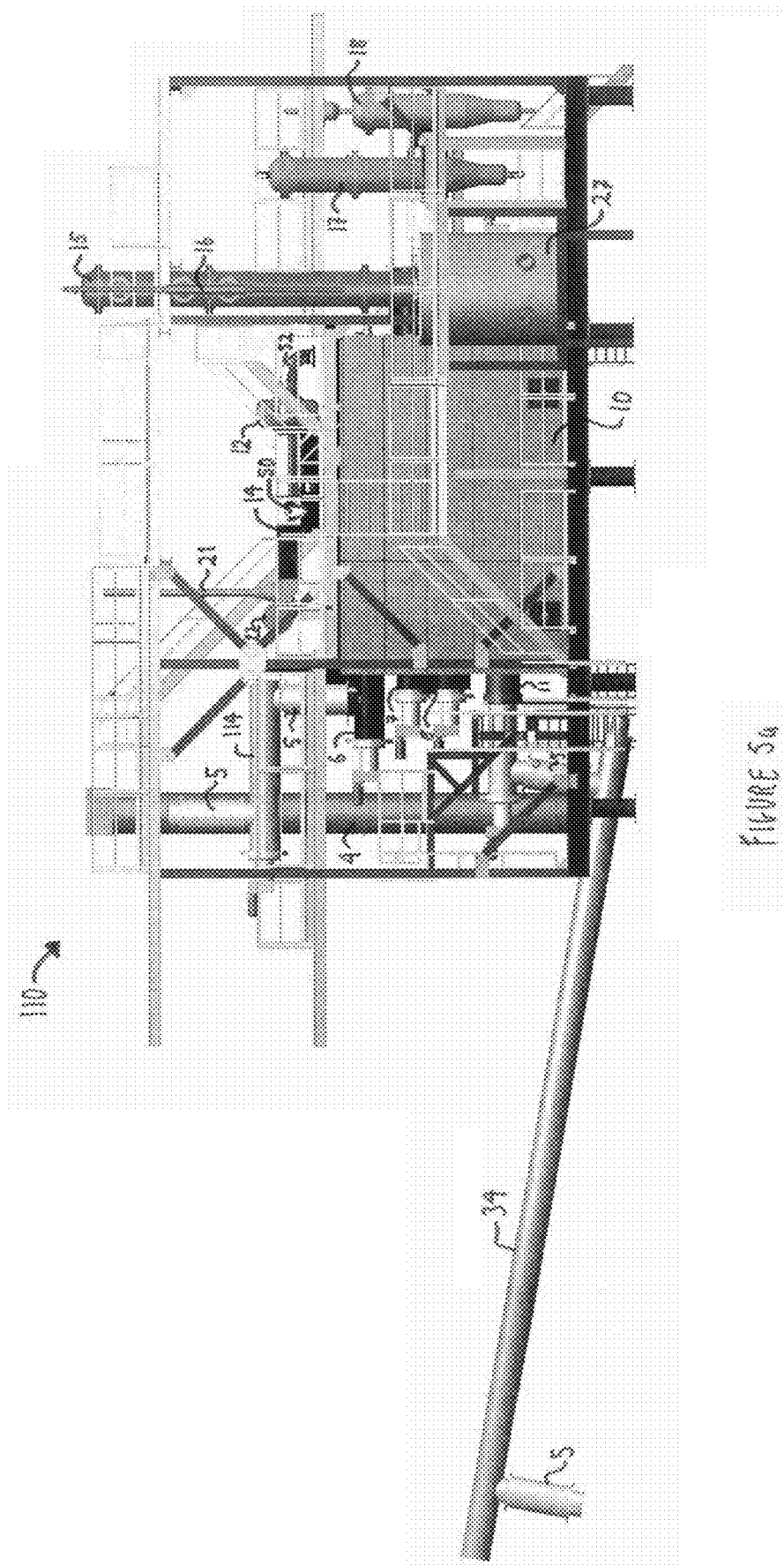

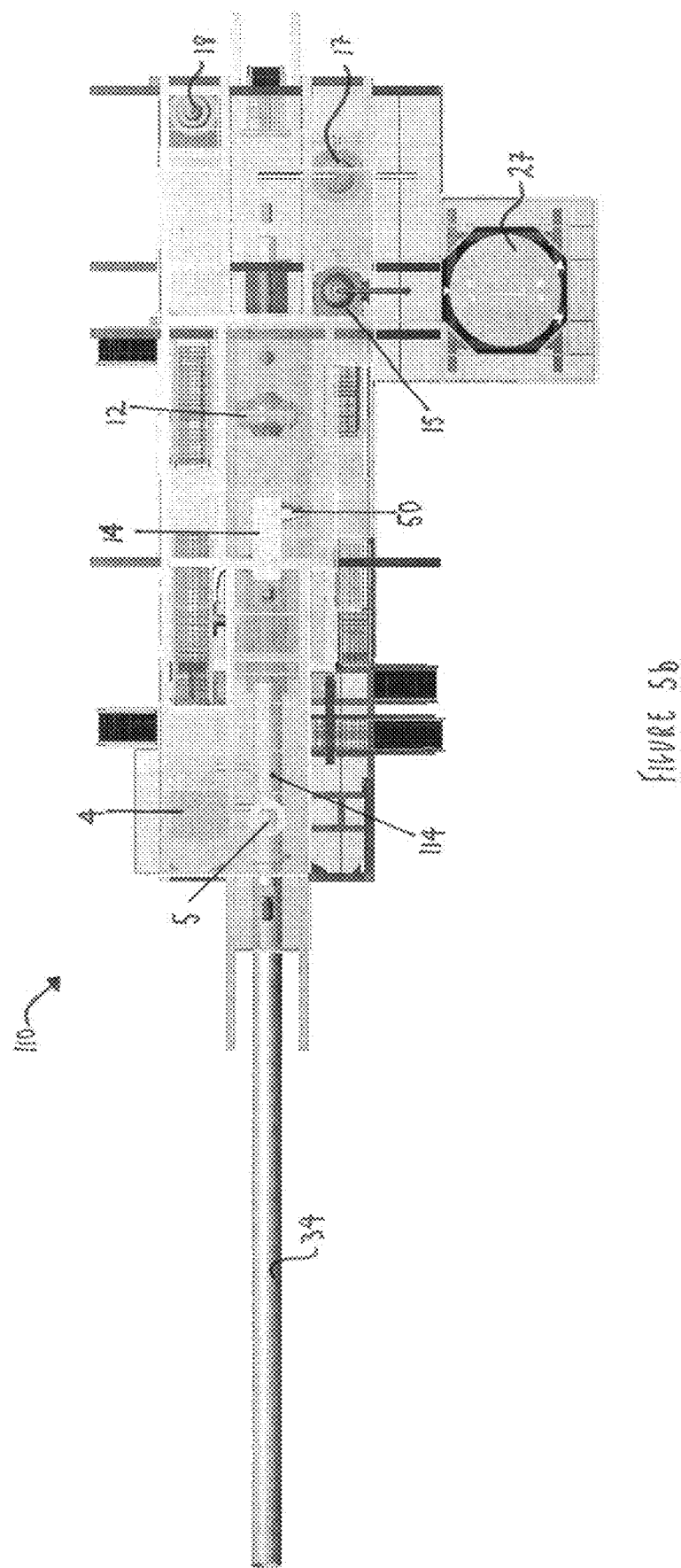

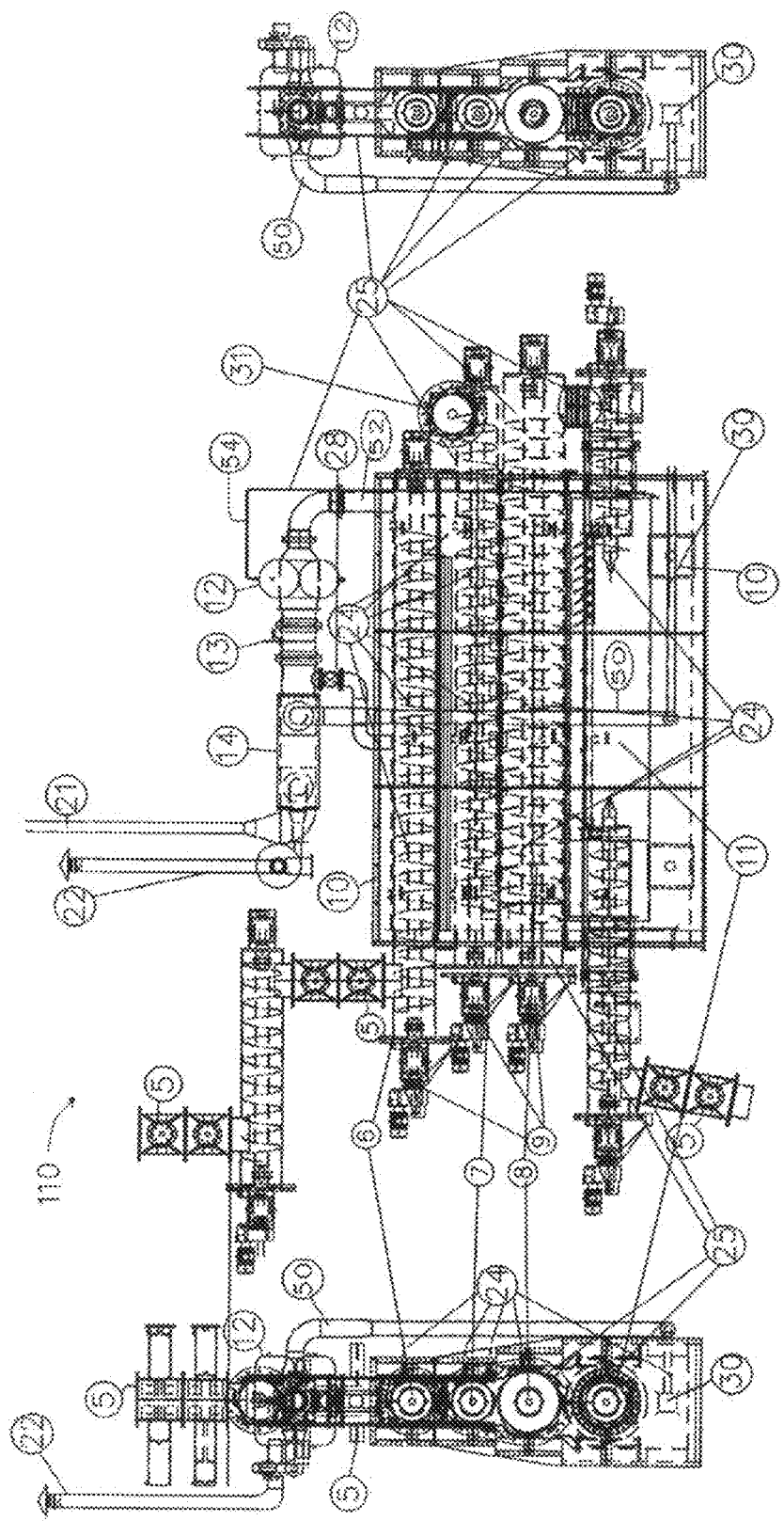

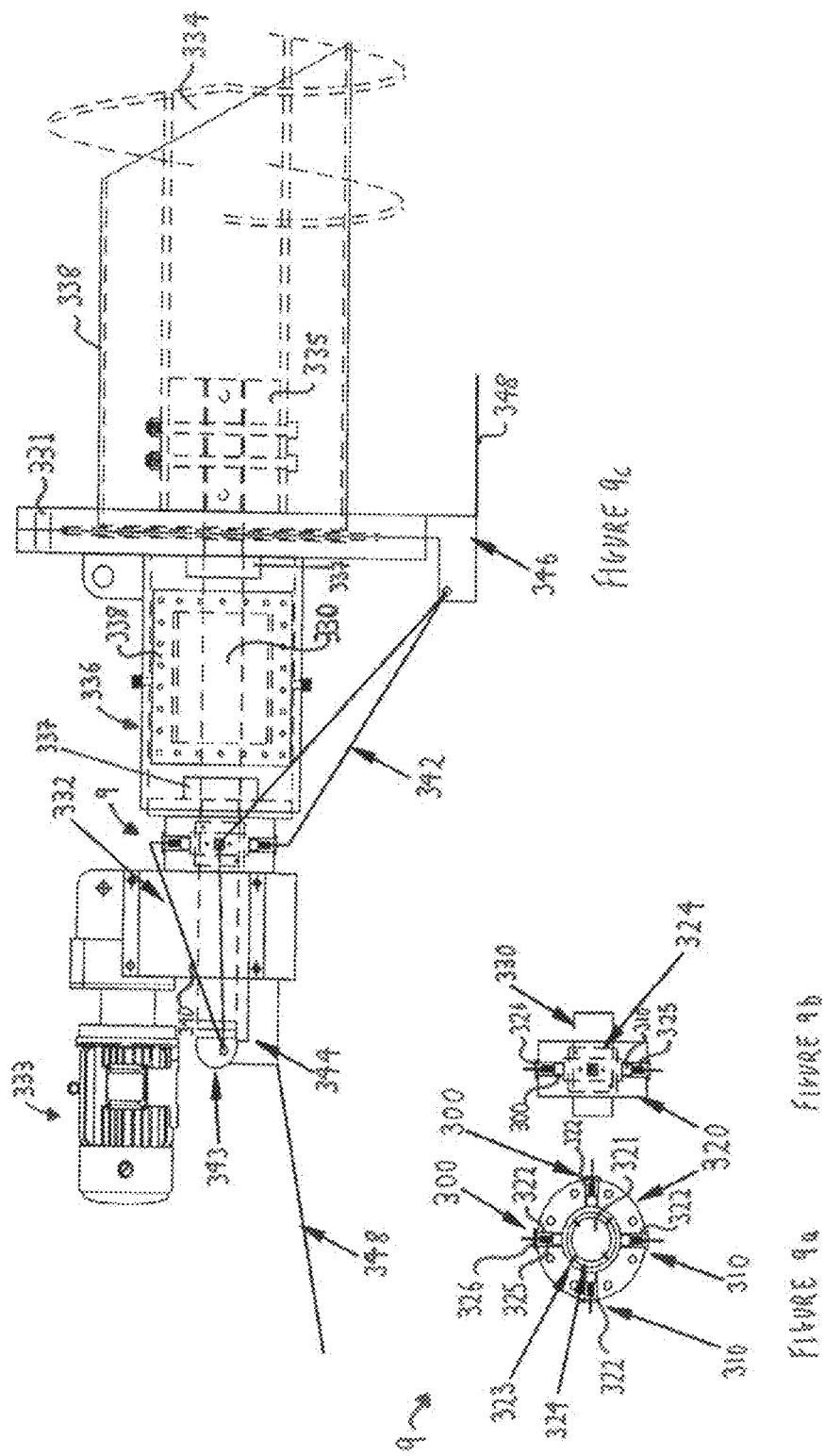

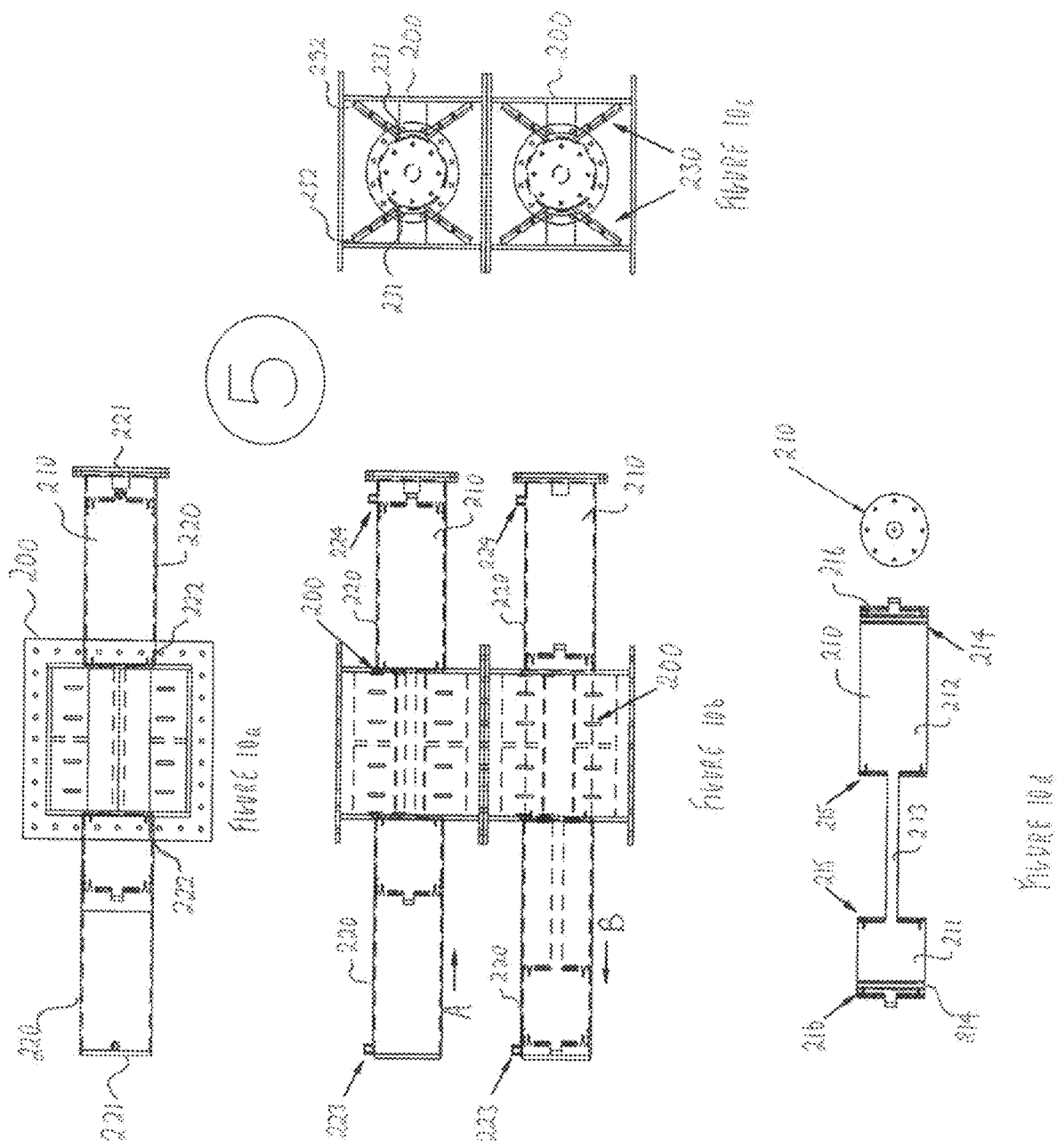

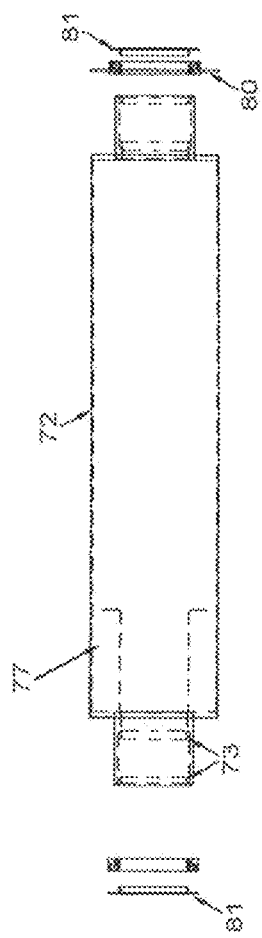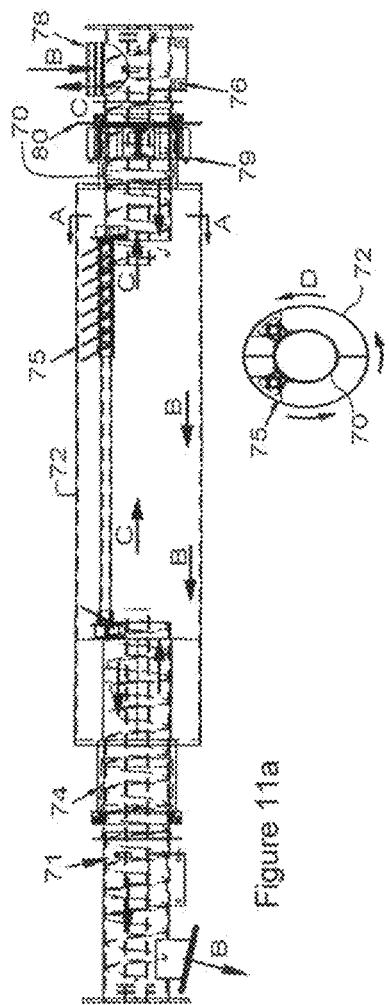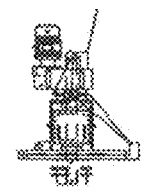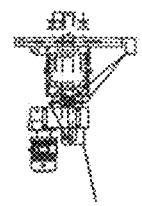

PROCESSING UNIT AND METHOD FOR SEPARATING HYDROCARBONS FROM FEEDSTOCK MATERIAL

RELATED APPLICATIONS

The present application is a continuation of U.S. application Ser. No. 14/396,892, filed Oct. 24, 2014, now abandoned, which is a national stage submission under 35 U.S.C. § 371 of International Application No. PCT/CA13/50318, filed Apr. 25, 2013, which claims the priority of Canadian Patent Application No. 2,775,338 filed Apr. 25, 2012, all of which are hereby incorporated by reference in their entireties.

TECHNICAL FIELD

The present disclosure is directed at a processing unit and method for separating hydrocarbons from feedstock material. More particularly, the present disclosure is directed at a processing unit and method for processing bitumen impregnated silica and clays into refined oil and gas.

BACKGROUND

Bitumen impregnated silica and clays are typically processed into refined oil and gas using Fischer-Tropsch process, retort systems, and alternative forms of solid distillation and pyrolysis. The most common of these processes, Fischer-Tropsch, has considerable environmental impact and uses large amounts of solvents and water as well as producing substantial amounts of green house gas.

Accordingly, research and development continues into systems and methods that can be used to extract hydrocarbons from hydrocarbon feedstock such as bitumen impregnated silica and clays which have less of an environmental impact.

SUMMARY

According to a first aspect, there is provided a processing unit for separating hydrocarbons from feedstock material. The processing unit includes at least one rotating conveyor in communication with a material inlet and a material outlet; a vacuum pump providing a vacuum atmosphere within the rotating conveyor; at least one material transfer device positioned at the material inlet and at least one material transfer device positioned at the material outlet, each material transfer device configured to allow transfer of feedstock material into or out of the rotating conveyor whilst maintaining the vacuum atmosphere within the rotating conveyor; and an electrostatic generator connected to the rotating conveyor providing a static charge to the vacuum atmosphere within the rotating conveyor.

The processing unit may also include a condenser in fluid communication with the rotating conveyor to receive and condense hydrocarbons separated from the feedstock material. One or more condensing columns may be utilized to condense the hydrocarbons separated from the feedstock material. The vacuum pump may work in unison with one of the condensing columns to provide gas scrubbing of the hydrocarbons.

Optionally the processing unit includes one or more steam injection valves for injecting steam into the vacuum atmosphere within the rotating conveyor. The steam may be injected at a temperature between about 200° C. to about 500° C. and a pressure between about 2 PSI to about 25 PSI.

The processing unit may also include a heated enclosure at least partially housing the rotating conveyor, in which heated fluid circulating within the heated enclosure transfers heat to the vacuum atmosphere within the rotating conveyor. A conduit may be positioned between the heated enclosure and a boiler to direct exhaust heated fluid exiting the heated enclosure to the boiler to aid production of steam. A boiler control valve may be positioned in fluid communication with the boiler, the boiler control valve being configured to open and release exhaust heated fluid to a heat exchanger when the boiler is operating in a steady state. The heat exchanger is configured to transfer remaining heat from exhaust fluid to intake fluid before it enters the heated enclosure. The fluid in the heated enclosure may be gas, such as air.

The processing unit may include a series of rotating conveyors with an increase in surface area for each of the conveyors in the series of rotating conveyors from the rotating conveyor nearest the material inlet to the rotating conveyor nearest the material outlet. The heated enclosure when present at least partially houses each of the rotating conveyors in the series of rotating conveyors, in which heated fluid circulating within the heated enclosure transfers heat to the vacuum atmosphere within each rotating conveyor. The heated enclosure may comprise a series of chambers, with each chamber housing a different rotating conveyor in the series of rotating conveyors, the temperature of each chamber being controllable to control the temperature of the vacuum atmosphere within each rotating conveyor in the series of rotating conveyors. The temperature of the vacuum atmosphere within each rotating conveyor may increase from the rotating conveyor nearest the material inlet to the rotating conveyor nearest the material outlet. The temperature within the heated enclosure may range from about 150° C. to about 450° C.

The processing unit may include an input conveyor for conveying feedstock material to the material inlet. A first material transfer device may be positioned at the entrance to the input conveyor and a second material transfer device may be positioned at the exit of the input conveyor. The processing unit may also include an output conveyor for conveying feedstock material away from the material outlet. As with the input conveyor, a first material transfer device may be positioned at the entrance of the output conveyor and a second material transfer device positioned at the exit of the output conveyor. The output conveyor may be rotated and cooled by a fluid. The cooling fluid may be water generated by the condensers during the hydrocarbon condensing process and recycled into a water receptacle. Steam generated by cooling the output conveyor may be combined with steam generated by the boiler for injection into the rotating conveyor.

The material transfer device may include a first sealing member including a first sealing body; a second sealing member including a second sealing body; a conduit having one or more side walls surrounding an internal passageway with opposed open ends, the side walls having a first pair of opposed apertures which receive the first sealing member and a second pair of opposed apertures which receive the second sealing member; a first housing for the first sealing member, the first housing secured to the side wall of the conduit surrounding and sealing the first pair of opposed apertures; and a second housing for the second sealing member, the second housing secured to the side wall of the conduit surrounding and sealing the second pair of opposed apertures. The first sealing member is movable in a transverse direction relative to the conduit from a closed position where the first sealing body is positioned within the internal passageway in sealing relationship with the side walls to provide a vacuum seal in the internal passageway of the conduit and an open position where the first sealing body is received in the first housing and is at least partially clear of the internal passageway to allow material to pass through the conduit. The second sealing member is movable in a transverse direction relative to the conduit from a closed position where the second sealing body is positioned within the internal passageway in sealing relationship with the side walls to provide a vacuum seal in the internal passageway of the conduit and an open position where the second sealing body is received in the second housing and is at least partially clear of the internal passageway to allow material to pass through the conduit. During use, the first or the second sealing member is in the closed position while the other of the first or second sealing member is in the open position to maintain a vacuum seal in the internal passageway of the conduit.

Transverse movement of the first and second sealing member from the open position to the closed position and vice versa may be through air actuation of the sealing member within the housing. The sealing relationship of the first sealing body and the second sealing body with the side walls of the conduit may be maintained by one or more seals positioned between the side walls and the first or second sealing body. The one or more seals may be seal plates extending between opposed side walls of the conduit with an outside edge in sealing contact with the side wall and an inside edge in sealing contact with the first or second sealing body. The first and second sealing member may be a cylinder. Optionally the cylinder may be a barbell shaped cylinder including two cylindrical bodies connected by a bar. In use, the bar is positioned within the internal passageway of the conduit when the cylinder is in the open position, and one of the cylindrical bodies is positioned within the internal passageway of the conduit when the cylinder is in the closed position.

The electrostatic generator may include a body with an aperture therein for receiving a shaft of the rotating conveyor; a bushing rotatably lining the aperture of the body; a pair of negatively charged magnets positioned within the body so that each negatively charged magnet contacts the bushing; a pair of positively charged magnets positioned within the body so that each positively charged magnet contacts the bushing; a first cable connecting each negatively charged magnet to either a drum or the shaft of the rotating conveyor; and a second cable connected each positively charged magnet to the other of the drum or the shaft of the rotating conveyor. In use, rotation of the conveyor shaft causes rotation of the bushing against the fixed negatively and positively charged magnets to produce a negative and positive charge which is transmitted to either the drum or the shaft of the rotating conveyor by the first or second cable respectively. The bushing may include an inner bushing and an outer bushing. The inner bushing may comprise polytetrafluoroethylene (Teflon™) and the outer bushing may comprise copper. The body may include four channels extending in a cross shape outwards from the aperture, with each channel housing a spring loaded magnet therein. The positively charged magnets are housed in two adjacent perpendicular channels while the negatively charged magnets are housed in the opposed two adjacent perpendicular channels.

According to another aspect, there is provided a material transfer device for transferring material whilst maintaining a vacuum in a system. The material transfer device includes a first sealing member including a first sealing body; a second sealing member including a second sealing body; a conduit having one or more side walls surrounding an internal passageway with opposed open ends, the side walls having a first pair of opposed apertures which receive the first sealing member and a second pair of opposed apertures which receive the second sealing member; a first housing for the first sealing member, the first housing secured to the side wall of the conduit surrounding and sealing the first pair of opposed apertures; and a second housing for the second sealing member, the second housing secured to the side wall of the conduit surrounding and sealing the second pair of opposed apertures. The first sealing member is movable in a transverse direction relative to the conduit from a closed position where the first sealing body is positioned within the internal passageway in sealing relationship with the side walls to provide a vacuum seal in the internal passageway of the conduit and an open position where the first sealing body is received in the first housing and is at least partially clear of the internal passageway to allow material to pass through the conduit. The second sealing member is movable in a transverse direction relative to the conduit from a closed position where the second sealing body is positioned within the internal passageway in sealing relationship with the side walls to provide a vacuum seal in the internal passageway of the conduit and an open position where the second sealing body is received in the second housing and is at least partially clear of the internal passageway to allow material to pass through the conduit. During use, the first or the second sealing member is in the closed position while the other of the first or second sealing member is in the open position to maintain a vacuum seal in the internal passageway of the conduit.

Transverse movement of the first and second sealing member from the open position to the closed position and vice versa may be through air actuation of the sealing member within the housing. The sealing relationship of the first sealing body and the second sealing body with the side walls of the conduit may be maintained by one or more seals positioned between the side walls and the first or second sealing body. The one or more seals may be seal plates extending between opposed side walls of the conduit with an outside edge in sealing contact with the side wall and an inside edge in sealing contact with the first or second sealing body. The first and second sealing member may be a cylinder. Optionally the cylinder may be a barbell shaped cylinder including two cylindrical bodies connected by a bar. In use, the bar is positioned within the internal passageway of the conduit when the cylinder is in the open position, and one of the cylindrical bodies is positioned within the internal passageway of the conduit when the cylinder is in the closed position.

According to another aspect, there is provided an electrostatic generator for providing a static charge to a rotating conveyor. The electrostatic generator may include a body with an aperture therein for receiving a shaft of the rotating conveyor; a bushing rotatably lining the aperture of the body; a pair of negatively charged magnets positioned within the body so that each negatively charged magnet contacts the bushing; a pair of positively charged magnets positioned within the body so that each positively charged magnet contacts the bushing; a first cable connecting each negatively charged magnet to either a drum or the shaft of the rotating conveyor; and a second cable connected each positively charged magnet to the other of the drum or the shaft of the rotating conveyor. In use, rotation of the conveyor shaft causes rotation of the bushing against the fixed negatively and positively charged magnets to produce a negative and positive charge which is transmitted to either the drum or the shaft of the rotating conveyor by the first or second cable respectively. The bushing may include an inner bushing and an outer bushing. The inner bushing may comprise polytetrafluoroethylene (Teflon™) and the outer bushing may comprise copper. The body may include four channels extending in a cross shape outwards from the aperture, with each channel housing a spring loaded magnet therein. The positively charged magnets are housed in two adjacent perpendicular channels while the negatively charged magnets are housed in the opposed two adjacent perpendicular channels.

According to another aspect, there is provided a method of separating hydrocarbons from feedstock material. The method includes rotating the feedstock material in at least one rotating conveyor in communication with a material inlet and a material outlet; providing a vacuum atmosphere within the rotating conveyor; providing a static charge to the vacuum atmosphere within the rotating conveyor; transferring the feedstock material into and out of the rotating conveyor through at least one material transfer device positioned at the material inlet and at least one material transfer device positioned at the material outlet, each material transfer device allowing transfer of feedstock material into or out of the rotating conveyor whilst maintaining the vacuum atmosphere within the rotating conveyor.

The method may also include condensing hydrocarbons separated from the feedstock material in a condenser in fluid communication with the rotating conveyor. Gas scrubbing of the hydrocarbons may also be provided.

Steam may optionally be injected into the vacuum atmosphere within the rotating conveyor. The steam may be injected at a temperature between about 200° C. to about 500° C. and a pressure between about 2 PSI to about 25 PSI.

The method may also include heating the vacuum atmosphere within the rotating conveyor through heat transfer from a heated fluid circulating within a heated enclosure at least partially housing the rotating conveyor. The exhaust heated fluid exiting the heated enclosure may be directed to a boiler to aid production of steam and to a heat exchanger to transfer heat from the exhaust heated fluid to intake fluid before it enters the heated enclosure. The temperature within the heated enclosure may range from about 140° C. to about 300° C.

The method may include conveying feedstock material to the material inlet using an input conveyor and conveying feedstock material away from the material outlet using an output conveyor. The output conveyor may be rotated and cooled by a fluid. The cooling fluid may be water and steam generated by the cooling process may be combined with steam generated by a boiler for injection into the rotating conveyor.

According to another aspect, there is provided a method of separating hydrocarbons from feedstock material using the processing unit described above.

BRIEF DESCRIPTION OF THE DRAWINGS

In the accompanying drawings, which illustrate one or more exemplary embodiments:

FIG. 4 shows a perspective view of the processing unit of FIG. 3.

FIG. 5a shows a side view of the processing unit of FIG. 4.

FIG. 5b shows a top view of the processing unit of FIG. 4.

FIG. 6a shows a side view of the heated enclosure of the processing unit of FIG. 3.

FIG. 6b shows an end view of the heated enclosure of the processing unit of FIG. 3.

FIG. 6c shows the opposite end view of the heated enclosure to that of FIG. 6b.

FIG. 7a shows the direction of flow in the heated enclosure depicted in FIG. 6a.

FIG. 7b shows the direction of flow in the heated enclosure depicted in FIG. 6b.

FIGS. 9a-c show an embodiment of the electrostatic generator of the processing unit of FIG. 3. FIG. 9a is a cross-sectional view of the electrostatic generator and FIG. 9b is a side view of the electrostatic generator. FIG. 9c shows the electrostatic generator connected to an auger of the processing unit.

FIGS. 10a-d show an embodiment of the material transfer device of the processing unit of FIG. 3. FIG. 10a is a top view of the material transfer device. FIG. 10b is a side view of the material transfer device. FIG. 10c is an end view of the material transfer device. FIG. 10d shows a side view and end view of the 'barbell' shaped cylinder of the material transfer device.

FIGS. 11a-c show an embodiment of the fourth rotating conveyor of the processing unit of FIG. 3. FIG. 11a is a side view of the fourth rotating conveyor with expanded ends. FIG. 11b is a cross sectional view through line A-A of FIG. 11a. FIG. 11c is a side view of the revolving core reactor of the forth rotating conveyor with expanded ends.

DETAILED DESCRIPTION

The embodiments described herein are directed at a method and system for processing hydrocarbons from hydrocarbon feedstock, such as coal, shale rock, and numerous waste materials for example sewage sludge, animal waste, trash, and solid industrial waste.

In one embodiment, a processing unit utilizes multiple apparatuses that work in unison with a thermal dynamic control system, which in turn communicates information to a hydrocarbon condensing phase to separate hydrocarbon gas from hydrocarbon feedstock material. The processing unit includes one or more rotating conveyors maintained under minimum vacuum. A static charge is generated in the vacuum atmosphere within the rotating conveyor by an electrostatic generator combined with rotational friction of the conveyor. The rotating conveyors may be indirectly heated using a multi chambered heated enclosure. The feedstock material travels within the thermal static vacuum atmosphere separated from the heat source by the conveyor walls. The rotating conveyors transport feedstock material through distinct temperature zones. The temperature zones are maintained as a result of the multi chambered heated enclosure and metered amounts of superheated steam injected into the rotating conveyors at a temperature of about 200° C. to about 500° C. and a pressure ranging from about 2 PSI to about 25 PSI. Thermal sensors located in different locations of the processing unit provide feed back for temperature control. Steam may be introduced to this statically charged atmosphere as required to both quench exothermic reactions and enhance endothermic reactions. Thermal statically charged hydrocarbon vapours are separated from the feedstock material and pass under vacuum into one or more condensers. In one embodiment, the hydrocarbon vapours, which are at temperatures ranging from 300° C. to 550° C., are instantly quenched in a 35° C. to 65° C. refluxed liquid Phase I Packing Column. Phase II condensing occurs in a 1° C. liquid chiller and in fluid communication with Phases III and IV. The condensed hydrocarbons that comprise highly aromatic fuel type oil, free flow into an oil water separator and the resulting oil is transported using pumps to bulk storage. The hydrocarbon free dry solid feedstock material may exits the rotating conveyors into an output conveyor at temperatures in excess of 370° C. to 480° C. The hot exiting material is cooled indirectly by water which produces steam. The steam may be combined with steam produced by a boiler, then super heated and introduced into the rotating conveyors. The cooled solids are ready for disposal or commercial use.

Directional terms such as "top," "bottom," "upwards," "downwards," "vertically" and "laterally" are used in the following description for the purpose of providing relative reference only, and are not intended to suggest any limitations on how any article is to be positioned during use, or to be mounted in an assembly or relative to an environment.

Figure 1:
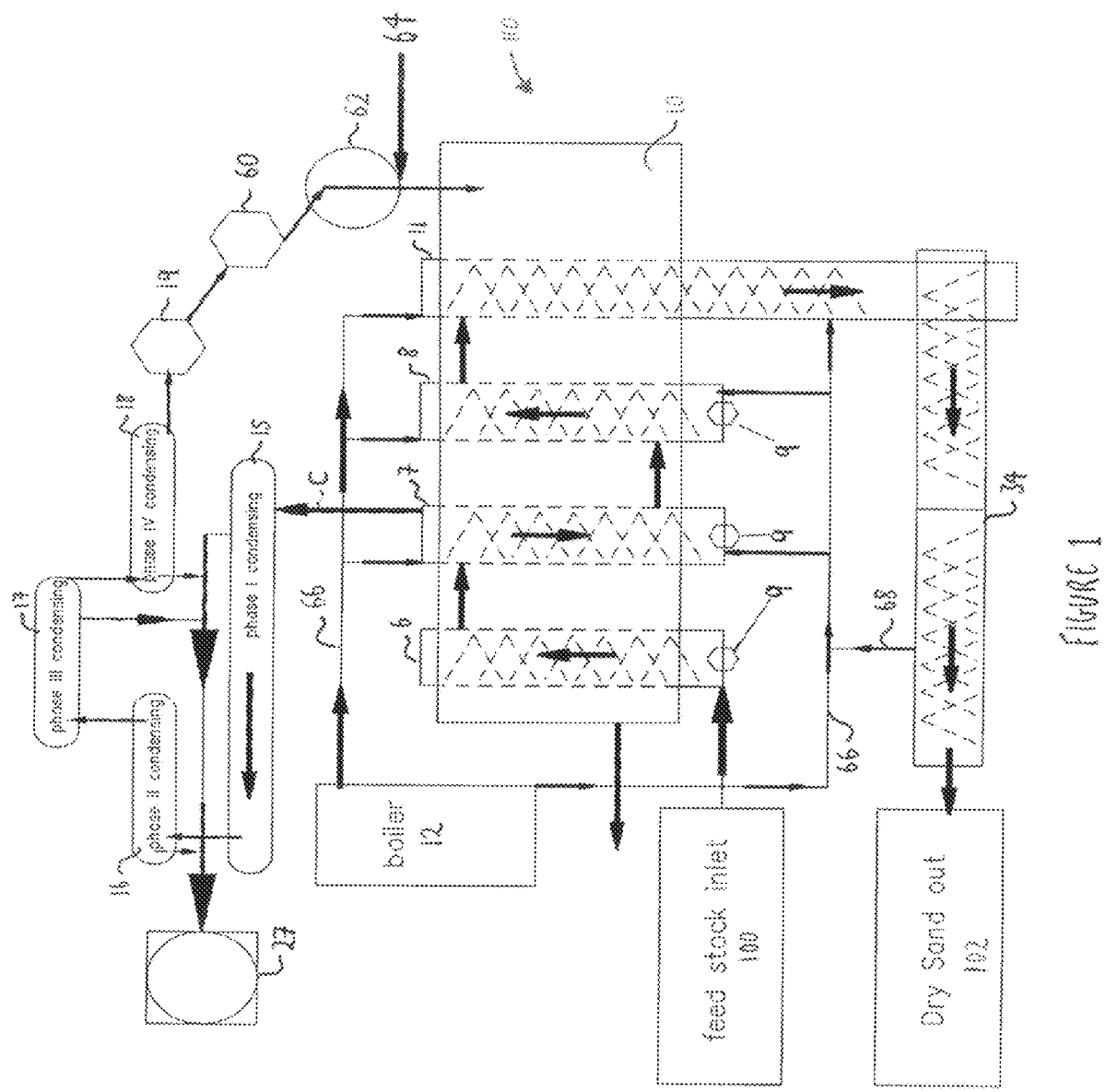
FIG. 1 shows a flow diagram of a system for processing hydrocarbon feedstock, according to an embodiment.

Referring now to FIG. 1, there is shown a schematic of a system for processing hydrocarbons from hydrocarbon feedstock. In FIG. 1, feedstock material is feed via a feedstock inlet 100 to a processing unit 110 comprising four rotating conveyors 6, 7, 8, 11 surrounded by a heated enclosure 10. The internal atmosphere in each rotating conveyor 6, 7, 8, 11 is maintained under vacuum. Vacuum is maintained at about 0.5 inches to 10 inches of water column using a vacuum pomp 19, such as, but not limited to, a liquid ring type vacuum pump. Rotating conveyors 6, 7, 8 are provided with an electrostatic generator 9 to provide a static charge to the atmosphere in the rotating conveyor. Superheated steam 66 may also be injected into one or more of the rotating conveyors through steam injection valves (not depicted). The feedstock material passes through each rotating conveyor 6, 7, 8, 11 in turn travelling under agitation within the thermal static vacuum atmosphere created by the static charge. Superheated steam may be introduced to this statically charged atmosphere as required to both quench exothermic reactions and enhance endothermic reactions. The heated enclosure 10 provides a heat source to heat the atmosphere within each rotating conveyor, while the conveyor walls provide a heat transferable barrier between the heat source and the thermal static vacuum atmosphere within each rotating conveyor.

Feedstock material flows through the conveyors 6, 7, 8, 11, 34 from the feedstock inlet 100 to the feedstock outlet 102 as a result of rotational movement of the conveyors. Hydrocarbon gas separated from the feedstock material flows in the opposite direction to the flow of feedstock material. The hydrocarbon gas is drawn out of conveyor 7 into a series of condensers 15, 16, 17, 18 under vacuum created by vacuum pump 19 (as shown by arrow C). The hydrocarbon gas is condensed in a series of condensing stages (Phase I to Phase IV condensing) provided by condensers 15, 16, 17, 18. The condensed hydrocarbons comprise a highly aromatic fuel type oil, which free flows into an oil and water separator 27 and the resulting oil may be transported via pumps (not shown) to bulk storage. Phase IV condensing may be carried out with a liquid ring gas scrubber in conjunction with vacuum pump 19 such that waste hydrocarbons, such as ethane, methane and some propane gases are released from the vacuum pump 19. The waste hydrocarbons may be processed further in gas processing unit 60 and blended with heat source gas 64 in a gas blender 62. The blended mixture of gases may be pumped into the heated enclosure 10, thereby reducing exhaust gases from the system. Conveyors 6, 7, 8, 11 are in fluid communication with condensers 15, 16, 17, 18, as well as oil and water separator 27 and vacuum pump 19. A vacuum is therefore maintained throughout the processing unit.

The dry and substantially hydrocarbon free feedstock material exits the processing unit 110 and passes along an output conveyor 34 and is transported away from the processing unit 110. Water or another liquid may be used to cool the exiting feedstock material and steam 68 created from the exit phase may be blended with steam generated from boiler 12 for injection into rotating conveyors 7, 8, 11 to minimize overall water consumption.

Figure 2:
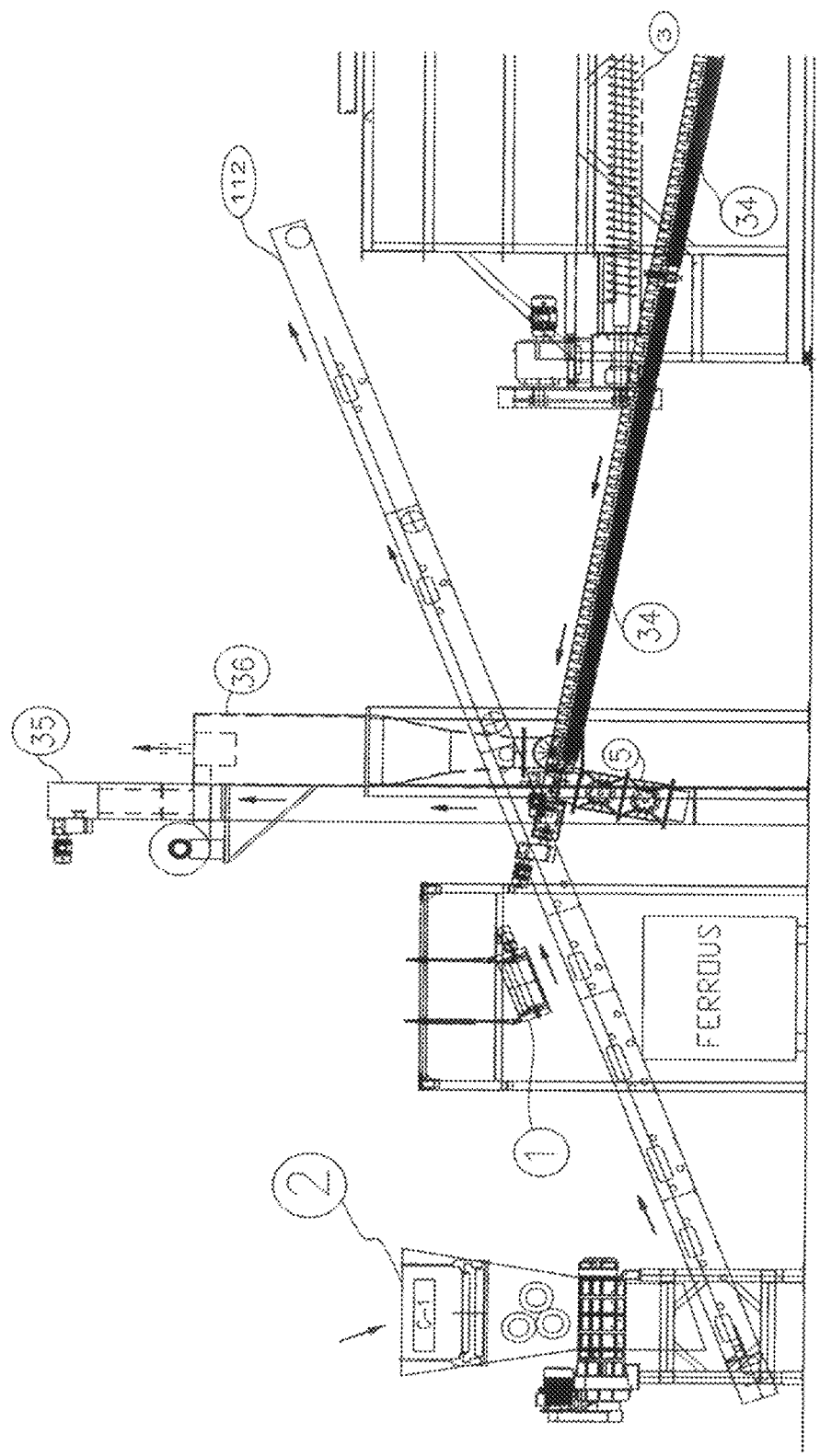
FIG. 2 shows the material inlet and material outlet sections of the system of FIG. 1.

Referring to FIG. 2, there is shown the feedstock inlet of the system. Hydrocarbon feedstock material, such as but not limited to, oil sands are trucked into a staging area and offloaded into a granulator 2. One or more conveyors (not shown) may be used to transport the hydrocarbon feedstock material to the granulator 2. The granulator 2 grinds down the feedstock material, such that only material of a predetermined maximum diameter enters the processing unit 110. The maximum predetermined diameter of the ground feedstock material may be between 5 mm to 30 mm or any diameter therebetween. Ground feedstock material exits the granulator 2 and is conveyed to a weigh hopper 3 by a conveyor 112. A cross belt magnet 1 may be positioned above the conveyor to remove ferrous material from the feedstock material. The weigh hopper 3 uses load cells to meter a predetermined programmed feed rate of ground feedstock material into a bucket elevator 4 (see FIG. 3). In alternative embodiments (not shown) the machinery used to transport the feedstock material into the processing unit 110 may differ from that shown in FIG. 2. Any combination of conveyors and optional granulators and magnets and the like may be used to convey the feedstock material into the processing unit.

Figure 3:
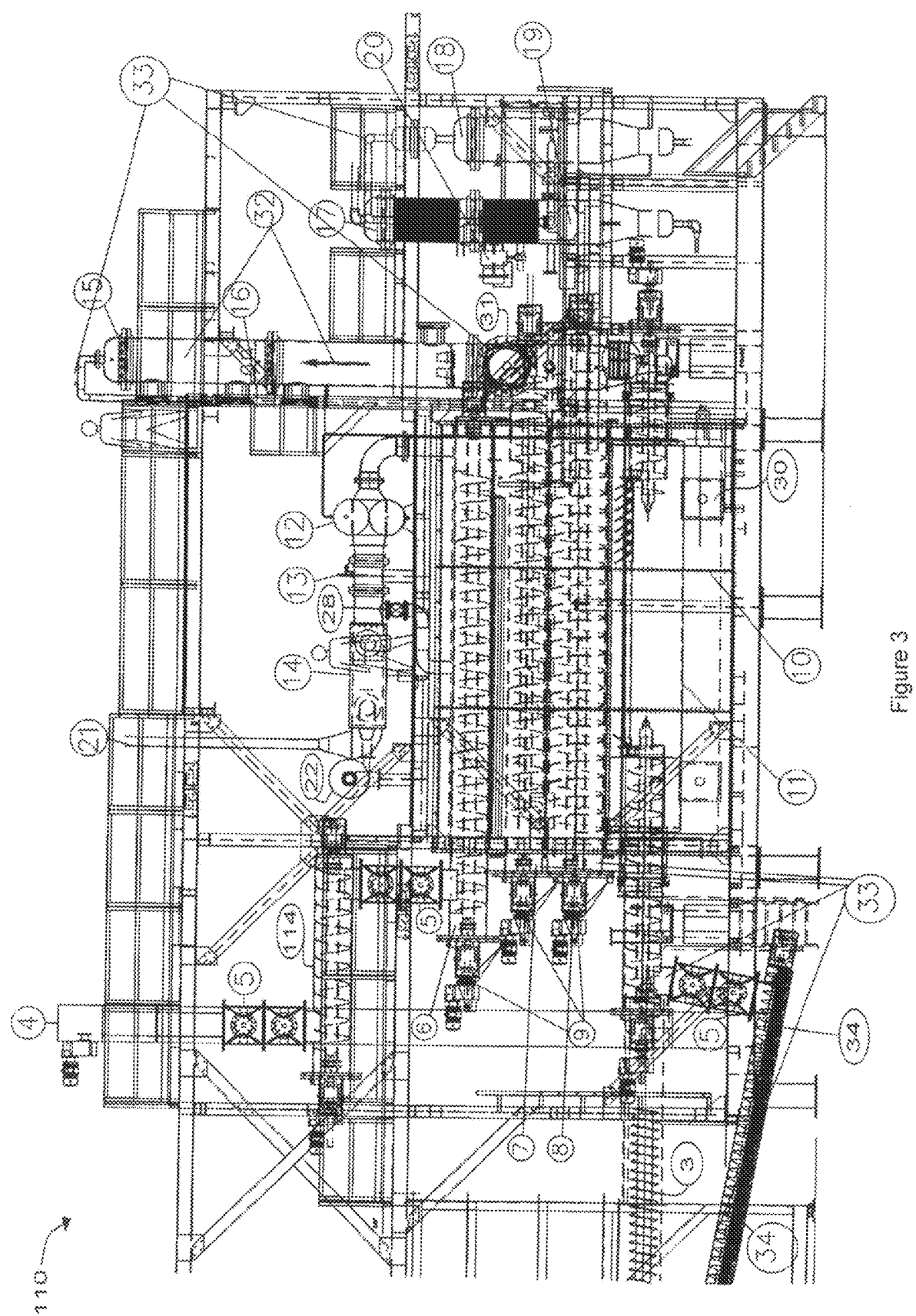
FIG. 3 shows the processing unit of the system of FIG. 1.
Figure 5C:
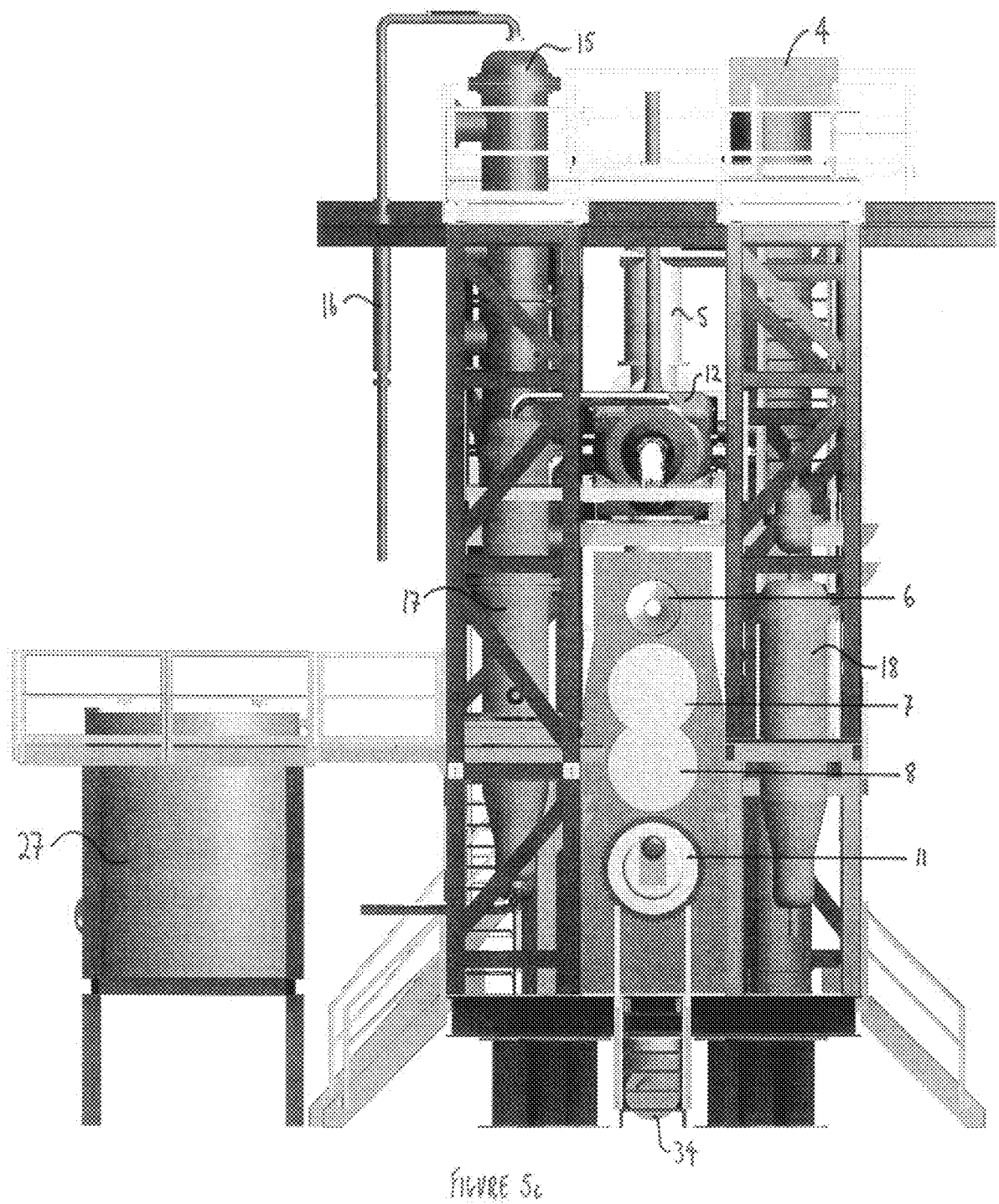
FIG. 5c shows an end view of the processing unit of FIG. 4.

Referring to FIGS. 3, 4 and 5, the bucket elevator 4 carries the ground feedstock material upwards and discharges it into a first material transfer device 5. The feedstock material passes through the first material transfer device 5 and along an input conveyor 114, then into a second material transfer device 5 before the feedstock material is transferred into the first rotating conveyor 6. The material transfer devices 5, together with additional material transfer devices 5 at the outlet end of the processing unit, allow feedstock material to be transferred into and out of the rotating conveyors 6, 7, 8, 11 whilst maintaining a vacuum atmosphere within the conveyors 6, 7, 8, 11. The arrangement of two spaced material transfer devices 5 for the input conveyor 114 performs a double redundancy for vacuum assurances. Further advantages are to allow the inlet feedstock material flow to equalize prior to entering the first rotating conveyor 6. In alternative embodiments (not shown) there may however be a single or a plurality of material transfer devices and any combination of conveyors which convey the feedstock material into the processing unit whilst maintaining a vacuum atmosphere within the processing unit.

One embodiment of a material transfer device 5 is shown in FIGS. 10a-d, which comprises two stacked box conduits 200 with a 'barbell' shaped cylinder 210 passing through each box conduit 200. Each box conduit 200 is open at the top and bottom ends thereof with closed side walls. An aperture in opposed side walls snugly receives the 'barbell' shaped cylinder 210. The 'barbell' shaped cylinder 210 has a shorter cylindrical section 211 connected to a longer cylindrical section 212 by a bar 213. In an alternative embodiment (not shown) the two cylindrical sections may be of identical length. Each cylinder 210 is encased in a cylinder housing which is made up of two cylindrical tubes 220 having a closed end 221 and an open end 222. The open end 222 of each cylindrical tube 220 is attached to the box conduit 200 by a series of bolts or the like, such that the cylindrical tube 220 surrounds and seals the aperture. In the side wall of the conduit. The two tubes 220 extend perpendicularly on either side of the box conduit 200 to enclose the cylinder 210. There is an air inlet 223, 224 in each cylindrical tube 220 near the closed end thereof 221 for air actuation of the cylinder 210 inside the cylindrical tubes 220 (as described in more detail below). An o-ring is positioned in grooves 214 near the outside end of each cylindrical sections 211, 212 to maintain a seal between the cylindrical section 211, 212 and the cylindrical tube 220. A wiper seal 215 is positioned on the inside edges of each cylindrical section, 211, 212. The wiper seals 215 may be made of Teflon™. Wear plates 216 are found on the outside end of each cylindrical section 211, 212. Four seal plates 230 extend between opposed side wall of the box conduit 200 (see FIG. 10c). The seal plates 230 are positioned with the inside edge 231 of each seal plate sealing the longer cylindrical section 212 of the cylinder 210 when it is positioned in the box conduit 200 and the outside edge 232 of each seal plate sealing the side wall of the box conduit 200 at, or approximate, each of the four corners of the box conduit. This arrangement maintains a vacuum seal between the longer cylindrical section 212 of the cylinder 210 and side walls of the box conduit 200 when the longer cylindrical section 212 is positioned in the box conduit 200. The seal plates may be made of naval brass and may be adjustable.

The 'barbell' shaped cylinders 210 move between an open position (as shown by arrow A in FIG. 10b) where the bar 213 of the cylinder 210 is positioned within the box conduit 200, and a closed position (as shown by arrow B in FIG. 10b) where the longer cylindrical section 212 is positioned within the box conduit 200. Movement of the cylinders 210 between the open and closed position is carried out by an air actuator (not shown) which may be controlled by a computer (not depicted). Air is introduced into air inlet 223 to move the cylinder 210 in direction A to the open position, whereas air is introduced into air inlet 224 to move the cylinder 210 in direction B to the closed position. When the cylinder 210 in one of the two stacked box conduit 200 is in open position A, the cylinder 210 in the other box conduit 200 will be in closed position B to maintain a vacuum seal at all times.

In use, the feedstock material is introduced into the top box conduit 200. The cylinder 210 in the top box conduit 200 is in open position A, whereas the cylinder 210 in the bottom box conduit 200 is in closed position B. This allows the feedstock material to fall through the top box conduit 200 under gravity until the material settles against the longer cylindrical section 212 positioned in the bottom box conduit 200. The cylinder 210 in the top box conduit 200 is then moved into closed position B before the cylinder 210 in the bottom box conduit 200 is moved into open position A. The feedstock material falls through the bottom box conduit under gravity. The feedstock material therefore passes through the material transfer device 5 in stages whilst maintaining a vacuum at all times.

Unlike conventional 'flapper' type gate valves or 'rotary vein' type material transfer devices, that periodically fail to seal properly due to materials being entrapped within the moving parts, the cylinder 210 actuates in a transverse plane only. The wiper plates 230 and wiper seals 215 clean the cylinders 210 as they actuate in a transverse direction, thereby minimizing or eliminating build up of materials within the moving parts and seals. This ensures that a tight vacuum seal is maintained.

From the first rotating conveyor 6, the dried feedstock material passes into a second rotating conveyor 7, and then into a third rotating conveyor 8 followed by a fourth rotating conveyor 11. The rotating conveyors 6, 7, 8, 11 may be a rotating drum, tube or auger like conveyor in which the feedstock material is rotated as it passes along the conveyor under vacuum. In one embodiment, the rotating conveyors 6, 7, 8, 11 are conventional screw-type augers rotated by a drive motor 333 and gear box 332 as shown in FIG. 9c. The rotating conveyors 6, 7, 8, 11 are arranged vertically and each passes through the heated enclosure 10, with the first rotating conveyor 6 at the top and the fourth rotating conveyor 11 at the bottom of the vertical stack. Each conveyor in the stack has an increased cross-sectional area, with the first rotating conveyor 6 having the smallest cross-sectional area and the fourth rotating conveyor 11 having the largest cross-sectional area, such that there is a surface area increase for each conveyor along the feedstock flow path. As the feedstock material passes through the series of rotating conveyors 6, 7, 8, 11, hydrocarbon gas is removed from the feedstock material. The concentration of hydrocarbon left in the feedstock material therefore decreases as the material passes through the processing unit 110; however the increase in surface area of each consecutive conveyor facilitates continuous removal of hydrocarbon gas from the feedstock material as the material passes along the feedstock flow path. In alternative embodiments (not shown) the number and set up of rotating conveyors may differ from that shown in FIGS. 3, 4 and 5. For example, there may be less than or more than four rotating conveyors which may be arranged in a different configuration within the heated enclosure.

The atmosphere within each rotating conveyor 6, 7, 8, 11 is maintained under vacuum. The vacuum parameters for the processing unit 110 may be between 0.5 to 10 inches of water column to allow sufficient retention time for the hydrocarbons to react together while they are in the rotating conveyors 6, 7, 8, 11. The cubic feet per minute (CFM) displacement at 0.5 to 10 inches of water column is between 10 to 25 CFM. Therefore the total CFM of the vacuum atmosphere of the rotating conveyors 6, 7, 8, 11 may be in excess of 1100 CFM and retention time of the feed stock material within this atmosphere may be between 10 to 12 minutes. Due to these ratios, an oversized vacuum pump may be needed with a pump orifice sized to properly evacuate the produced gas volumes at this low displacement. The type of vacuum pump and size of pump orifice required will be readily apparent to a person of skill in the art.

In one embodiment, vacuum parameters are maintained by a computer (not depicted) which receives feedback from a plurality of vacuum sensors 33 located throughout the processing unit 110. The sensors 33 detect inches of water column which may range from 0 inches of water column by the sensor located at the exit of the forth rotating conveyor 11, to 20 inches of water column by the sensor located closest to the vacuum pump 19. The process vacuum parameters may be set by the computer taking the sum total of all the vacuum sensor inputs and setting an average set point, which in turn controls a pneumatically actuated valve 20 and the revolutions per minute (RPM) of the vacuum pump. The computer program may detect variants from location to location and adjust automatically to assure a constant state of vacuum equilibrium. The program may also build a data base and profile of all the vacuum leak points. Once thresholds are breached beyond process parameters the computer tells the operators what locations require service. While the foregoing discusses one exemplary embodiment for providing a vacuum within the system, alternative embodiments (not depicted) are possible and would be apparent to a person of skill in the art. For example a different vacuum pump and pump control set up may be used to control the vacuum pressure in the processing unit.

Figures 7A, 7B:
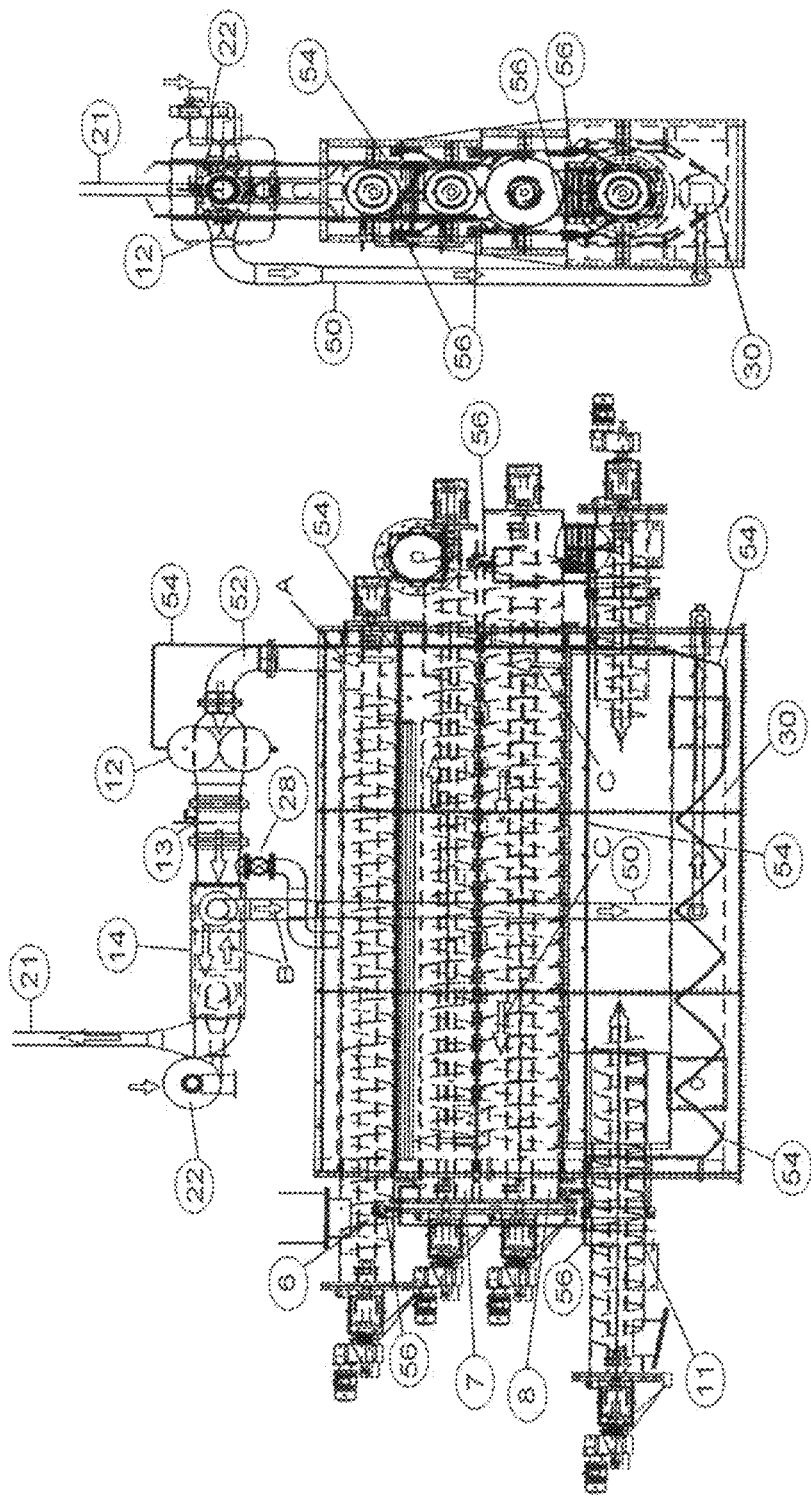

The temperature of each rotating conveyor 6, 7, 8, 11 is controlled and may increase from the first rotating conveyor 6 to the fourth rotating conveyor 11. Referring to the embodiment shown in FIGS. 3, 6 and 7, the heated enclosure comprises a plurality of panels (not shown) with a number of distinct chambers that allow heated turbulent air flow to continually oscillate against the outer walls of the rotating conveyors 6, 7, 8, 11. The heated air may flow in one direction along the bottom of the rotating conveyors and in the opposite direction along the top of the rotating conveyors. This zig zag type oscillation controls heat absorption through the conveyor walls into the vacuum atmosphere within the rotating conveyors. In addition, there may be smaller connecting plates (not shown) within the heated enclosure 10 set at specific angles, which add further turbulence against the conveyor tube walls. At start up of the processing unit 110 a heat source 30 is initiated by natural gas, propane or an alternate fuel type. Air is drawn into an air intake 22 and metered to promote optimum combustion. Air from the air intake 22 is drawn down the processing unit through pipe 50 and heated by the heat source 30. The heated enclosure 10 begins to slowly heat all the chambers proportional to the distance from the heat source 30 and the ratio of heat absorption through the thickness of the conveyor walls (see FIG. 7). The fourth rotating conveyor 11 stays in revolutionary motion during the start up sequence due to it close proximity to the heat source 30 to prevent structural failure. The direction of flow of heated air within the heated enclosure 10 is shown in FIG. 7a and indicated as arrows C. Thermal sensors 24 positioned throughout the processing unit provide feedback to allow automatic adjustment of the fuel to air ratio during start up. The temperature range of the chambers of the heated enclosure 10 is controlled via a programmed dampening valve 28 together with a boiler control valve 13 that regulate the upper temperature zones of the heated enclosure 10. To achieve the operating temperature zones of the internal atmosphere of the rotating conveyors 6, 7, 8, 11, the temperature zones of the external heated air of the heated enclosure may maintain a proportional temperature variant of about 140° C. to about 600° C. This relationship of indirect heating of the internal atmosphere of the rotating conveyors 6, 7, 8, 11 as heat is absorbed through the conveyor wall is maintained throughout operation of the processing unit. In one embodiment the ratio of cubic meters of air within the heated enclosure 10 external to the conveyors and the cubic meters of air in the vacuum atmosphere in the rotating conveyors 6, 7, 8, 11, are substantially equal. This allows for accurate control of proportional heating values of absorption from external heated air in the heated enclosure to the internal heated air in the rotating conveyors. Thermal sensors 24 are strategically placed throughout the heated enclosure housing and inserted into the conveyor walls and/or through the conveyor shafts to accurately control the heated enclosure temperature.

In one embodiment the walls of the conveyors 6, 7, 8, 11 may include a first layer of insulated high temperature wool, a second layer of refractory block and a third innermost layer of standard "bakery oven" refractory. The innermost (third) refractory layer may be a custom blend that dries white and is therefore reflective. This coupled with the close proximity of the feedstock material to the conveyor walls results in less energy required for maintaining temperature control.

Heated exhaust air exits the heated enclosure 10 and passes along tube 52 to a boiler 12 (as indicated by arrow A in FIG. 7a). The heated exhaust air thus aids production of super heated steam by the boiler 12. The programmable boiler control valve 13 remains partially closed until the boiler 12 begins producing steam. Once the boiler produces steam and is operating in a 'steady state', the boiler control valve 13 opens to allow the heated exhaust air to enter an air to air heat exchanger 14. Air from the air intake 22 passes through the air to air heat exchanger 14 prior to entering tube 50 and being directed to heat source 30 (as indicated by arrows B in FIG. 7b). Heat is transferred from the exhaust air to the intake air in the air to air heat exchanger 14. The intake air passing into tube 50 may therefore be at a temperature between 90° C. to 150° C. The exhaust air exiting the processing unit 110 via exhaust 21 has therefore had much of its heat removed and is typically of a temperature between 38° C. and 65° C. This alignment of components enables the processing unit 110 to maximize all the potential heat sources and thereby reduces energy costs.

Referring to FIGS. 7a and 7b, steam is generated by boiler 12 and passes along steam line 54 which enters the heated enclosure 10 and coils around heat source 30. Heat from the heat source 30 causes the steam to become superheated to a temperature of about 200° C. to about 500° C. The superheated steam is transporting to the rotating conveyors 6, 7, 8, 11 by steam line 54. Steam injection valves 56 control the input of steam into the conveyors. The steam injection valves 56 may be programmable air actuated valves which receive feedback regarding temperature, pressure and flow rate from sensors 25 positioned within the steam lines (see FIGS. 6a and 6b). The injection valves 56 control injection of steam at a pressure of between about 2 PSI to about 25 PSI until a 'steady state' is reached.

One or more of the rotating conveyors 6, 7, 8, 11 is fitted with an electrostatic generator 9 for pulsing a controlled charge through the internal atmosphere of each conveyor. An embodiment of the electrostatic generator 9 is shown in FIGS. 9a-c. In this embodiment, a direct current (DC) is generated by a pair of negatively charged magnets 300 and a pair of positively charged magnets 310. Referring to FIGS. 9a and 9b a cylindrical body or coupler 320, which may be made of Teflon™, has an aperture 321 therethrough and four channels 322 which extend from the aperture to the outer surface of the coupler dissecting the coupler like a cross. Lining the wall of the aperture is an outer bushing 323 and an inner bushing 324. The outer bushing 323 may be made of copper and the inner bushing 324 may be made of Teflon™. The pair of negatively charged magnets 300 are positioned within two perpendicular channels 322 and the pair of positively charged magnets 310 are position within the two opposed perpendicular channels 322. Each magnet 300, 310 is pressed against the surface of the outer bushing 323 by a spring 325. A cap 326 seals off the interior of each channel 322 to prevent dust and the like from entering the channel 322.

FIG. 9c shows an embodiment of the electrostatic generator 9 connected to a rotating conveyor comprising a conventional screw-type auger. The electrostatic generator 9 is positioned at one end of the auger. An auger shaft 330 passes out through an end plate 331 of the auger and is connected at one end to a gear box 332, which in turn is connected to a motor 333. The motor 333 and the gear box 332 act to rotate the auger shaft 330. The other end of the auger shaft 330 is connected to the main auger shaft 334 by a connector 335, so that rotational movement of the auger shaft 330 translates into rotation of the auger. A vacuum chamber 336 is positioned externally of the auger adjacent the end plate 331. The vacuum chamber 336 comprises two vacuum shaft seals 337 surrounding the auger shaft 330 at either end of the chamber 336, with one of the vacuum shaft seal 337 positioned adjacent the end plate 331 and the other vacuum shaft seal 337 positioned adjacent the electrostatic generator 9. An access panel 338 with tapped bolt holes therein allows access to adjust the two vacuum seals 337 as required, as the vacuum atmosphere may escape from time to time due to expansion and contraction of the conveyor. The electrostatic generator is positioned between the vacuum chamber 336 and the gear box 332 with the auger shaft 330 passing through the aperture 321. As the auger shaft 330 rotates, there is rotation of the inner and outer bushing 323, 324 of the electrostatic generator 9, whereas the coupler 320 (with the magnets 300, 310 therein) remains fixed in place. Rotation of the bushing 323, 324 against the fixed magnets 300, 310 produces a negative charge from the pair of negative magnets 300 and a positive charge from the pair of positive magnets 310. An electrical cable 340 connects each positive magnet 310 to a current coupler 343 which is attached to the auger shaft 330 to provide a positive charge to the auger shaft 330 which in turn is passed to the main auger shaft 334. The current coupler 343 is attached to a positive capacitor and amplitude controller 344. Another electrical cable 342 connects each negative magnet 300 to a negative capacitor and amplitude controller 346 which is connected to the auger end plate 331 to provide a negative charge to the auger tube wall 338. Each of the positive and negative capacitor and amplitude controllers 344, 346 may be connected to a computer (not shown) via a cable 348 to enable a user to control the amount of current entering the auger. The electrostatic generator 9 controls and enhances the electrostatic relationship that naturally occurs between the feedstock material and the rotational friction of the auger. The electrostatic generator of this embodiment therefore beneficially uses rotation of the screw-type auger to generate an electrostatic charge.

The first rotating conveyor 6 may be a drying conveyor that removes moisture from the hydrocarbon feedstock material. The moisture content of the hydrocarbon feedstock material may be in excess of 10% and high moisture content could alter retention time and reduce throughput capabilities. Removal of moisture from the feedstock material therefore increases productivity. The operating temperature of the first (drying) conveyor 6 may range from about 120° C. to about 260° C. The first rotating conveyor 6 may be equipped with an electrostatic generator 9 to provide a static charge to the vacuum atmosphere within the conveyor 6. The electrostatic generator 9 of the first conveyor 6 may or may not be operational dependent on feedstock moisture content and hydrocarbon content.

Once the feedstock material has passed through the first rotating conveyor 6, which may take about 3 to 5 minutes depending on moisture content, the material falls into the second rotating conveyor 7. The operating temperature of the second rotating conveyor 7 may range from about 280° C. to about 350° C. The second rotating conveyor 7 is also equipped with an electrostatic generator 9 to provide a static charge to the vacuum atmosphere within the second rotating conveyor 7. In addition, superheated steam is injected under low pressure into the second rotating conveyor 7 via one or more steam injection valves 56. Within the second rotating conveyor 7 the pressure of injected steam may range from about 1 PSI to about 10 PSI and the injected steam may have a temperature between about 150° C. to about 250° C. and a flow rate of about 0.37 kilograms per minute to about 1.8 kilograms per minute. The second rotating conveyor 7 provides both static charge and agitation to the feedstock material, such that the feedstock material is tossed against the hot walls of the conveyor and electrostatically charged, so as to release hydrocarbons from the feedstock material. When superheated steam enters the atmosphere within the second rotating conveyor 7, the static charge disassociates the hydrogen molecules from oxygen such that between 25% to 65% of the total volume of steam input is separated into hydrogen and oxygen. This provides extra hydrogen for producing between 10% and 25% higher volumes of separated hydrocarbons than is produced in the absence of steam. Without wishing to be bound by theory, it is believed that this methodology also produces enough oxygen within the vacuum atmosphere of the conveyors to provide the impetus for chemical reactions to occur while supplying enough steam to aid in the stripping phase of hydrocarbon degradation.

The feedstock material exits the second rotating conveyor 7 and drops into the third rotating conveyor 8. The material that is now in the third rotating conveyor 8 is subjected to a gain in surface contact due to the increased size of the third rotating conveyor 8, which may have between 20-40% gain in surface area compared to the second rotating conveyor 7. The third rotating conveyor 8 is also provided with an electrostatic generator 9 and low pressure steam is injected into rotating conveyor 8 via one or more steam injection valves 56. The same proportional temperature and thermal static relationships are at play as in the second rotating conveyor 7, but the threshold of these parameters is increased as the amount of hydrocarbon content in the feedstock material has decreased. The thermal static vacuum atmosphere within the third rotating conveyor 8 is regulated based on thermal sensory feedback and initial ratios of moisture content and hydrocarbon content of the feedstock material. The operating temperature within the third rotating conveyor 8 may be between about 315° C. to about 400° C. Steam input parameters may also increase, such that steam injected into the third rotating conveyor 8 is at a pressure of about 3 to about 12 PSI, temperature of between about 150° C. and 450° C. and volume between about 0.5 kilograms per minute and 2 kilograms per minute.

The feedstock material passes from the third rotating conveyor 8 to the fourth rotating conveyor 11. The fourth rotating conveyor 11 has an increased surface contact area compared to the third rotating conveyor 8, such as between 10-30% increased surface contact area. In one embodiment as shown in FIGS. 11a-c, the fourth rotating conveyor 11 includes an entrance auger 70, an exit auger 71 and a revolving core reactor 72 made of a hardened steel alloy that is resistant to heat and abrasion. The core reactor 72 revolves in the direction of arrow D (FIG. 11b) around both the entrance auger 70 and the exit auger 71 as a result of a drive sprocket 80 and 2 piece flange bearing 79 positioned at the entrance end of the core reactor 72. The entrance auger 70 may remain stationary at the drive end (entrance end) 76 to allow for horizontal expansion when heated. Two spaced seals 73, such as navel brass seals, are positioned at each end of the revolving core reactor 72 to maintain a vacuum seal with the entrance auger 70 and exit auger 71. A void 74 between the revolving core reactor 72 and each of the entrance auger 70 and exit auger 71 is filled with packing material compressed in place by a packing retaining ring 81. The packing material may be graphite impregnated rope packing, which forms a triple redundant vacuum seal that will expand and contract with the revolving core reactor 72. An expansion joint 78 is welded to the entrance auger 70.

The fourth rotating conveyor 11 may be at a slight downward tilt, such as about a 2-5° tilt, so as to take advantage of fluid dynamics and gravity. The feedstock material moves downhill in the direction of arrows B and is lifted by internal baffles 77 at the exit end of the revolving core reactor 72 and transferred to the exit auger. The temperature in the fourth rotating conveyor 11 has again increased compared to the third rotating conveyor 8, and the operating temperature range may be between about 390° C. to 480° C. Superheated steam is injected into the entrance auger 70 and the exit auger 71 by one or more steam injection valves (not shown), at a temperature of about 150° C. to 450° C., pressures between about 10 PSI and 20 PSI and volume between about 1.5 kilograms per minute and 5 kilograms per minute.

Feedstock material entering the fourth rotating conveyor 11 typically has less than 40% hydrocarbon content. The feedstock material at this stage has highly electrostatic properties, as a result of transportation through the statically charged atmosphere of the second and third rotating conveyors 7, 8 and optionally the first rotating conveyor 6. The wall of the revolving core reactor 72 may have a temperature in excess of 550° C. due to the proximity of the wall to the heat source 30 of the heated enclosure 10. The high wall temperature combined with the thermal static vacuum atmosphere within the revolving core reactor 72 may result in coking. Internal scrappers 75 minimize the coking effect. As the core reactor 72 revolves the stationary scrapper 75 remove deposited coke material. The revolving core reactor 72 may be of sufficient size that operators can enter the reactor for inspection. This allows the internal scrappers 75 to be strategically placed and maintained to minimize coking issues within the revolving core reactor 72. Frictional rotation of the core reactor surface leads to release of all, or substantially all, of the remaining hydrocarbons from the feedstock material. The hydrocarbon vapour travels under vacuum in the direction of arrows C and passes into the third rotating conveyor 8 and then into the second rotating conveyor 7. Without wishing to be bound by theory, it is believed that since the atomic valance bond of silica and the carbon atom are virtually identical, the natural counter effects of agitated positive and negative ions from these atomic structures, enhanced by static charge, results in complete, or substantially complete, hydrocarbon extraction from virtually any hydrocarbon based feedstock material regardless of the type of natural bond entrapment.

The dry and hydrocarbon free, or substantially hydrocarbon free feedstock material exits the fourth rotating conveyor 11 and passes into the output conveyor 34 through one or more material transfer device 5 as shown in FIG. 3. The material transfer device 5 allows the exiting feedstock material to pass into the output conveyor 34 whilst maintaining the vacuum atmosphere within the rotating conveyor 11. The exiting feedstock material may have a temperature of from about 370° C. to about 425° C. In order to cool the hot exiting feedstock material to a manageable temperature, the output conveyor 34 may be cooled with a cooling fluid such as water. Rotation of the output conveyor 34 brings the hot exiting feedstock material into contact with the wall of the output conveyor 34. Baffling on the exterior of the output conveyor wall (not shown) moves the cooling fluid at a 180 degree radial motion such that heat transfers from the hot solid feedstock material touching the conveyor wall to the external cooling fluid. It is important to cool the solid feedstock material leaving the processing unit 110 as carbon black remains in an activated state at a temperature above 100° C. Carbon black in its activated state wants to combine with hydrogen and can therefore become volatile when exposed to the atmosphere. Steam created from the exit phase may be blended with steam generated from boiler 12 for injection into the rotating conveyors 7, 8 and 11 to minimize overall water consumption as shown in FIG. 1.

Referring to FIG. 2, the exiting feedstock material passes out of the output conveyor 34 through a further material transfer device 5 to a bucket elevator 35. The hydrocarbon free feedstock material may then be loaded into a cyclone separator 36 for further separation of the solid particles which may be transported away from the processing unit 110. In alternative embodiments (not shown) there may be a single or a plurality of material transfer devices 5 and any combination of conveyers and other equipment which conveys the feedstock material out of the processing unit 110 whilst maintaining a vacuum atmosphere within the processing unit 110.

Figure 8:
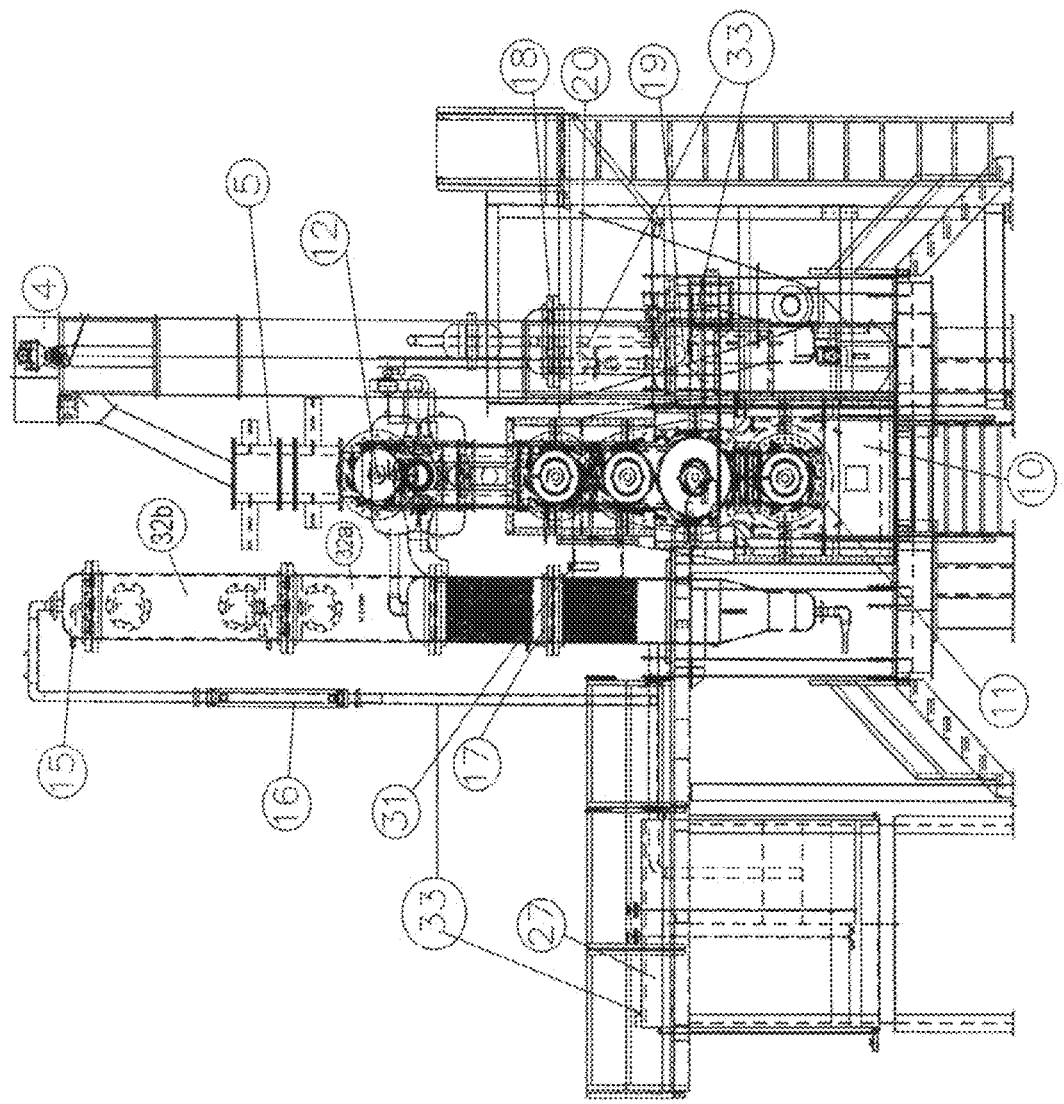
FIG. 8 shows the hydrocarbon condensing area of the processing unit of FIG. 3.

In one embodiment as shown in FIGS. 3 and 8, separated hydrocarbon gas flows under vacuum and exits the second rotating conveyor 7 into a Phase I condensing column 15. The column 15 may be positioned within one meter of the exiting hydrocarbon vapours. The exiting hydrocarbon vapours are statically charged and may be at a temperature between 340° C. and 450° C., which is generally cooler than current processes. The hydrocarbon vapours pass through a fluidized particulate filter 31 before entering the Phase I condensing column 15, so as to suppress particles from being drawn into the Phase I condensing column 15. The hydrocarbon vapours travel upwards via vacuum into a first packing chamber 32a and then upward to the second packing chamber 32b. Each packing chamber 32a, 32b has a fluid reflux line injected above the packing. This fluid pumps from either an oil water separator 27 or an alternative source. The dual fluid injection locations allows for temperature control of each section. Cooler water or warm process fuel oil can flow alternately depending on process parameters. The fluid flows downwards through the packing under gravity and the hydrocarbons are vacuumed upwards through the packing. Alternate packing may be used in each packing chamber 32a, 32b dependent on desired fuel oil quality. In this embodiment, 65% to 80% of the hydrocarbons condense at Phase I. Phase II condensing is carried out by a water chilled tube type condenser 16. A Phase III condenser 17 is of the same basic design as the Phase I condenser 15, but with denser packing. Phase I condenser 15, Phase II condenser 16 and Phase III condenser 17 each share a common pipe header that allows for the condensed hydrocarbons to flow freely to the oil water separator 27. The oil water separator 27 separates the condensed liquid hydrocarbons from water, with most of the water being present as a result of the steam injected into the rotating conveyors. In one embodiment vacuum pump 19 is located in unison with a Phase IV condenser 18. Phase IV condenser 18 works in unison with the vacuum pump 19 to provide final phase gas scrubbing of the hydrocarbons.

Waste hydrocarbon gases extracted during the process include ethane, methane and some propane gases. The amount of waste gas is dependent on feedstock type, for example the waste gas of oil sands may average 4-8% of the percentage of total hydrocarbons found within the formation. Waste gas exits via a vacuum control valve 20 and are processed further using one or more gas processing units 60 (as shown in FIG. 1) and blended with heat source gas 64 in a gas blender 62. The blended mix of gases is pumped into the heated enclosure 10 and used to heat the heated enclosure, thereby reducing exhaust gases from the system. During production, waste hydrocarbon gas may represent up to 25% of total gas required to heat the heated enclosure. For example, coal waste gas contributes up to 35% of the total gas required in the heated enclosure, while shale rock waste gas may be up to 50% total gas required.

While the foregoing discusses one exemplary embodiment for condensing hydrocarbons and dealing with waste hydrocarbon gases, alternative embodiments (not depicted) are possible and would be apparent to a person of skill in the art. For example, the number and types of condensers may be different and alternative hydrocarbon condensing methods may be used as known in the art.

The estimated extraction time for the majority of any hydrocarbon based feedstock material is 10 to 12 minutes. Depending on the feedstock hydrocarbon content and moisture content a capacity of 2 to 10 metric tones per hour can be achieved. The output of the processing unit may be scaled up by either combining multiple processing units or by increasing the size and capacity of the processing unit. The processing conditions of a larger processing unit generally remain substantially constant, such as surface area contact, time and distance, amplitude input and temperature thresholds. The larger processing unit would, however, require increased horse power to move the increased volume of feedstock material, increased volume of steam, as well as increased horse power to handle the increased air flow (cubic feet per minute) of the vacuum while maintaining the same vacuum velocity.

When thermal sensors 24 within the processing unit 110 indicate an excessive exothermic reaction, programming protocols automatically adjust and compensate steam, heat input and material flow to compensate. This also occurs during an endothermic reaction. This orchestrated methodology of multiple input parameters leads to a steady state. When a steady state is achieved, the maximum feed rate as it relates to oil sands may be about 4 to 5 metric tonnes with the parameters described above. Once 'steady state' processing parameters are reached, the processing unit may be maintained with less than 500,000 BTU's per hour. It is also anticipated that a scalability factor of 4 to 1 can be achieved with future up scaling.

Oil produced by the processing unit may be 88% to 98% aromatic with a pour point of −25° C. to −38° C. The processing unit beneficially extracts bitumen and converts up to 99.5% of the hydrocarbon content into a fuel oil and process gas, while using only one barrel of water for every four barrels of oil produced. The only emission from the processing unit is exhaust gas from the heated enclosure having a temperature that is typically below 40° C. The process requires no solvents or addition of catalysts. There is also none of the excessive heating and waste material of existing techniques. Natural gas consumption is less than 5% of the BTU per hour, as the amount of the BTU per hour equivalent of the fuel oil produced. Alternative feedstock material with higher hydrocarbon content, for example tires, utilize less than 1% of the required heat source gas of the total amount of BTU per hour equivalent of the fuel oil produced. The processing unit therefore has less environment impact than commonly used processes, such as Fischer-Tropsch. Furthermore, no up graders are needed and no tailing ponds and the dry sand or carbon black exiting the processing unit can be reclaimed.

While particular embodiments have been described in the foregoing, it is to be understood that other embodiments are possible and are intended to be included herein. It will be clear to any person skilled in the art that modification of and adjustments to the foregoing embodiments, not shown, are possible.

The invention claimed is:

1. A processing unit for separating hydrocarbons from feedstock material, the processing unit comprising:
    (a) at least one rotating conveyor in communication with a material inlet and a material outlet;
    (b) a vacuum pump providing a vacuum atmosphere within the rotating conveyor;
    (c) at least one material transfer device positioned at the material inlet and at least one material transfer device positioned at the material outlet, each material transfer device configured to allow transfer of feedstock material into or out of the rotating conveyor whilst maintaining the vacuum atmosphere within the rotating conveyor; and
    (d) an electrostatic generator configured to generate a static charge in the vacuum atmosphere through rotation of the rotating conveyor.

2. The processing unit of claim 1, further comprising a condenser in fluid communication with the rotating conveyor to receive and condense hydrocarbons separated from the feedstock material.

3. The processing unit of claim 1, further comprising one or more steam injection valves for injecting steam into the vacuum atmosphere within the rotating conveyor.

4. The processing unit of claim 1, further comprising a heated enclosure at least partially housing the rotating conveyor, wherein heated fluid circulating within the heated enclosure transfers heat to the vacuum atmosphere within the rotating conveyor.

5. The processing unit of claim 1, wherein the at least one rotating conveyor is a series of rotating conveyors with an increase in surface area for each of the conveyors in the series of rotating conveyors from the rotating conveyor nearest the material inlet to the rotating conveyor nearest the material outlet.

6. The processing unit of claim 5, further comprising a heated enclosure at least partially housing each of the rotating conveyors in the series of rotating conveyors, wherein heated fluid circulating within the heated enclosure transfers heat to the vacuum atmosphere within each rotating conveyor.

7. The processing unit of claim 6, wherein the heated enclosure comprises a series of chambers, with each chamber housing a different rotating conveyor in the series of rotating conveyors, the temperature of each chamber being controllable to control the temperature of the vacuum atmosphere within each rotating conveyor in the series of rotating conveyors.

8. The processing unit of claim 1, further comprising an input conveyor for conveying feedstock material to the material inlet and an output conveyor for conveying feedstock material away from the material outlet.

9. The processing unit of claim 8, wherein
(i) a first input material transfer device is positioned at an entrance to the input conveyor and a second input material transfer device is positioned at an exit from the input conveyor; and
(ii) a first output material transfer device is positioned at an entrance to the output conveyor and a second output material transfer device is positioned at an exit from the output conveyor.

10. The processing unit of claim 1, wherein the material transfer device comprises:
(a) a first sealing member comprising a first sealing body;
(b) a second sealing member comprising a second sealing body;
(c) a conduit having one or more side walls surrounding an internal passageway with opposed open ends, the side walls having a first pair of opposed apertures which receive the first sealing member and a second pair of opposed apertures which receive the second sealing member;
(d) a first housing for the first sealing member, the first housing secured to the side wall of the conduit surrounding and sealing the first pair of opposed apertures; and
(e) a second housing for the second sealing member, the second housing secured to the side wall of the conduit surrounding and sealing the second pair of opposed apertures,
wherein the first sealing member is movable in a transverse direction relative to the conduit from a closed position where the first sealing body is positioned within the internal passageway in sealing relationship with the side walls to provide a vacuum seal in the internal passageway of the conduit and an open position where the first sealing body is received in the first housing and is at least partially clear of the internal passageway to allow material to pass through the conduit, and the second sealing member is movable in a transverse direction relative to the conduit from a closed position where the second sealing body is positioned within the internal passageway in sealing relationship with the side walls to provide a vacuum seal in the internal passageway of the conduit and an open position where the second sealing body is received in the second housing and is at least partially clear of the internal passageway to allow material to pass through the conduit, the first or the second sealing member being in the closed position while the other of the first or second sealing member is in the open position to maintain a vacuum seal in the internal passageway of the conduit.

11. The processing unit of claim 1, wherein the electrostatic generator comprises:
(a) a body with an aperture therein for receiving a shaft of the rotating conveyor;
(b) a bushing rotatably lining the aperture of the body;
(c) a pair of negatively charged magnets positioned within the body so that each negatively charged magnet contacts the bushing;
(d) a pair of positively charged magnets positioned within the body so that each positively charged magnet contacts the bushing;
(e) a first cable connecting each negatively charged magnet to either a drum or the shaft of the rotating conveyor; and
(f) a second cable connected each positively charged magnet to the other of the drum or the shaft of the rotating conveyor.

12. A method of separating hydrocarbons from feedstock material, the method comprising:
(a) rotating the feedstock material in at least one rotating conveyor in communication with a material inlet and a material outlet;
(b) providing a vacuum atmosphere within the rotating conveyor; and
(c) generating a static charge in the vacuum atmosphere using an electrostatic generator;
(d) transferring the feedstock material into and out of the rotating conveyor through at least one material transfer device positioned at the material inlet and at least one material transfer device positioned at the material outlet, each material transfer device allowing transfer of feedstock material into or out of the rotating conveyor whilst maintaining the vacuum atmosphere within the rotating conveyor,
wherein the electrostatic generator generates the static charge through rotation of the rotating conveyor.

13. The method of claim 12, further comprising condensing hydrocarbons separated from the feedstock material in a condenser in fluid communication with the rotating conveyor.

14. The method of claim 12, further comprising injecting steam into the vacuum atmosphere within the rotating conveyor.

15. The method of claim 14, wherein the steam is injected at a temperature between about 200° C. to about 500° C. and a pressure between about 2 PSI to about 25 PSI.

16. The method of claim 12, further comprising heating the vacuum atmosphere within the rotating conveyor through heat transfer from a heated fluid circulating within a heated enclosure at least partially housing the rotating conveyor.

17. The method of claim 16, wherein the temperature within the heated enclosure is from about 140° C. to about 600° C.

18. The method of claim 12, further comprising conveying feedstock material to the material inlet using an input conveyor and conveying feedstock material away from the material outlet using an output conveyor.

19. The method of claim 18, wherein the output conveyor is rotated and cooled by a fluid.

20. A method of separating hydrocarbons from feedstock material using the processing unit of claim 1.

* * * * *